US008685951B2

(12) United States Patent
Basnakian et al.

(10) Patent No.: US 8,685,951 B2
(45) Date of Patent: Apr. 1, 2014

(54) COMPOSITIONS AND METHODS FOR CYTOPROTECTION

(75) Inventors: Alexei G. Basnakian, Little Rock, AR (US); Richard B. Walker, North Little Rock, AR (US); John R. J. Sorenson deceased, Little Rock, AR (US); Anne S. Martin, legal representative, Tallahassee, FL (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 1187 days.

(21) Appl. No.: 12/055,790

(22) Filed: Mar. 26, 2008

(65) Prior Publication Data

US 2009/0042850 A1 Feb. 12, 2009

Related U.S. Application Data

(60) Provisional application No. 60/908,339, filed on Mar. 27, 2007.

(51) Int. Cl.
*A61K 31/555* (2006.01)
*C07F 3/06* (2006.01)
(52) U.S. Cl.
USPC ............................ 514/181; 548/101; 556/118
(58) Field of Classification Search
USPC ............................ 514/181; 548/101; 556/118
See application file for complete search history.

(56) References Cited

U.S. PATENT DOCUMENTS 5,846,988 A 12/1998 Hellberg
2006/0105972 A1 5/2006 Nagasawa

OTHER PUBLICATIONS

Atzei et al. "IR, NMR, XPS studay of 1-(D-3-mercapto-2-methylpropionyl)L-proline and its zinc complexes" Spectrochimica Acta, 1992, pp. 911-919.*
Sorenson et al. "Radiation protection and radiation recovery with essential metalloelement chelates" Procedings of the Society for Experimental Biology and Medicine, 1995, pp. 191-204.*
Floersheim et al. "Differential radioprotection of bone marrow and tumour cells by zinc aspartate" The British Journal of Radiology, 1988, pp. 501-508.*
Kawase et al. "Liver Protection by Bis(Maltolato)Zinc(II) Complex" Experimental Animals, 2004, vol. 53, pp. 1-9.*
Bichay et al., "Modification of survival and hematopoiesis in mice by tocopherol injection following irradiation", Strahlentherapie und Onkologie, 1986, pp. 391-399, vol. 162, No. 6.

Nagasawa et al., "2-Substituted thiazolidine-4(R)-carboxylic acids as prodrugs of L-cysteine. Protection of mice against acetaminophen hepatotoxicity", Journal of Medicinal Chemistry, 1984, pp. 591-596, vol. 27, No. 5.
Napirei et al., "Features of systemic lupus erythematosus in Dnase 1-deficient mice", Nature Genetics, 2000, pp. 177-181, vol. 25, No. 2.
Roberts et al., "Mechanisms of Chemoprotection by Ribcys, A Thiazolidine Prodrug of L-Cysteine", Medicinal Chemistry Research, 1991, pp. 213-219, vol. 1.
Zhou et al., "Synthesis and Radioprotective Effect of Zinc(II) Complexes with Cysteamine, Cysteine and Mercaptopropionylglycine"; Pharmacy and Pharmacology Communications; 2000; p. 299-302; vol. 6.
Atzei et al., "IR, NMR, XPS study of 1-(D-3-mercapto-2-methylpropionyl)-L-proline and its zinc complexes", Spectrochimica Acta, Part A: Molecular and Biomolecular Spectroscopy; 1992; pp. 911-919; vol. 48A; No. 7.
Floersheim et al., "Further studies on selective radioprotection by organic zinc salts and synergism of zinc aspartate with WR 2721"; The British Journal of Radiology; 1990; pp. 468-475; vol. 63; No. 750.
Floersheim et al., "Differential radioprotection of bone marrow and tumour cells by zinc aspartate"; The British Journal of Radiology; 1988; pp. 501-508; vol. 61, No. 726.
Floersheim et al., "Protection against ionizing radiation and synergism with thiols by zinc aspartate", The British Journal of Radiology; 1986; pp. 597-602; vol. 59; No. 702.
Limson et al., "The interaction of melatonin and its precursors with aluminium, cadmium, copper, iron, lead and zinc: an adsorptive voltammetric study"; Journal of Pineal Research; 1998; pp. 15-21; vol. 24; No. 1.
Krishnankutty et al., "Metal chelates of curcuminoids", Synthesis and Reactivity in Inorganic Chemistry; 1998; pp. 1313-1325; vol. 28, No. 8.
Samuni et al., "The use of Zn-desferrioxamine for radioprotection in mice, tissue culture, and isolated DNA"; Cancer Research; 1999; pp. 405-409; vol. 59.
Sharma et al., "Biological evaluation, chelation and molecular modeling studies of novel metal-chelating inhibitors of NF-kappaB-DNA binding: structure activity relationships", Journal of Medicinal Chemistry; 2006; pp. 3595-3601; vol. 49; No. 12.
Sorenson et al., "Cu, Fe, Mn, and Zn chelates offer a medicinal chemistry approach to overcoming radiation injury"; Current Medicinal Chemistry; 2002; pp. 639-662; vol. 9, No. 6.
Sorenson et al., "Radiation protection and radiation recovery with essential metalloelement chelates", Proceedings of the Society for Experimental Biology and Medicine; 1995; pp. 191-204; vol. 210, No. 3.
Bandyopadhyay et al., "Reactive oxygen species: Oxidative damage and pathogenesis", Current Science, Sep. 10, 1999; pp. 658-666; vol. 77, No. 5.

* cited by examiner

*Primary Examiner* — Joseph Kosack
(74) *Attorney, Agent, or Firm* — Polsinelli PC

(57) ABSTRACT

The present invention provides compositions and methods for cytoprotection. In particular, it provides zinc chelate compositions comprising at least one zinc ion and at least one aminothiol ligand.

23 Claims, 17 Drawing Sheets
(12 of 17 Drawing Sheet(s) Filed in Color)

COMPOSITIONS AND METHODS FOR CYTOPROTECTION

CROSS REFERENCE TO RELATED APPLICATIONS

This application claims the priority of U.S. provisional application No. 60/908,339, filed Mar. 27, 2007, which is hereby incorporated by reference in its entirety.

GOVERNMENTAL RIGHTS

This invention was made with government support under RadCCORE grant (5 U19 AI-067798) awarded by the National Institutes of Health. The government has certain rights in the invention.

FIELD OF THE INVENTION

The invention relates to compositions and methods for protecting cells from cellular injuries. In particular, the compositions and methods provide protection against injuries that increase the levels of reactive oxygen species in a cell.

BACKGROUND OF THE INVENTION

Many cellular injuries, such as exposure to ionizing radiation, result in the production of reactive oxygen species (ROS). These ROS produce a spectrum of damage via multiple mechanisms including membrane destabilization, mitochondrial disruption, and metabolic derangement. Furthermore, these ROS may activate endonucleases by inducing their synthesis and release from cellular compartments, thereby, allowing nuclear import of endonucleases and DNA degradation. DNA damage induced by endonucleases is several orders of magnitude greater than the direct damage by ROS. The peak of endonucleases activity usually follows oxidative stress by several hours, induces apoptotic cell death, and then declines in a few days.

While there are native antioxidant enzymes that convert ROS to water and oxygen, these systems are not always sufficient, however. Thus, there is a need for strategies to augment these systems and provide greater protection. Furthermore, there are currently no pharmaceutical compositions that directly target and inhibit cell death endonucleases. Thus, there is a current need for compositions that have the ability to inhibit the activity of cell death endonucleases by a variety of mechanisms.

SUMMARY OF THE INVENTION

Among the various aspects of the present invention is one that provides a first zinc chelate compound. The compound comprises at least one $Zn^{2+}$ ion and at least one ligand, wherein a compound of formula (I) is a source of the ligand. The compound of formula (I) comprises:

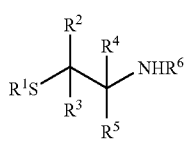
(I)

wherein:
  $R^1$ is selected from the group consisting of hydrogen, phosphate, and acyl; and
  $R^2$, $R^3$, $R^4$, $R^5$, and $R^6$ are independently selected from the group consisting of hydrogen, hydrocarbyl, and substituted hydrocarbyl.

Another aspect of the invention provides a second zinc chelate compound. The compound comprises at least one $Zn^{2+}$ ion and at least one ligand, wherein a compound of formula (II) is a source of the ligand. The compound of formula (II) comprises:

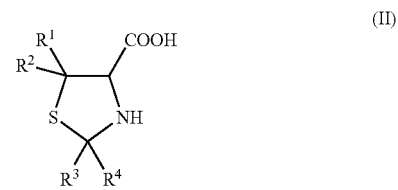
(II)

wherein:
  $R^1$ and $R^2$ are independently selected from the group consisting of hydrogen, hydrocarbyl, and substituted hydrocarbyl, wherein $R^1$ and $R^2$ together may form a group selected from the group consisting of =O, =S, and a hydrocarbyl ring comprising from three to six members; and
  $R^3$ and $R^4$ are independently selected from the group consisting of hydrogen, hydrocarbyl, and substituted hydrocarbyl, wherein $R^3$ and $R^4$ together may form a group selected from the group consisting of =O, =S, and a hydrocarbyl ring comprising from three to six members.

Yet another aspect of the invention encompasses a method for protecting a cell from a cellular injury. The method comprises contacting the cell with a composition comprising a nuclease inhibitor and an antioxidant.

A further aspect of the invention provides a method for radioprotection of a cell. The method comprises contacting the cell that is subject to an ionizing radiation with a zinc chelate of an aminothiol. The zinc chelate has endonuclease inhibitor activity and antioxidant activity.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION

Figure 2:
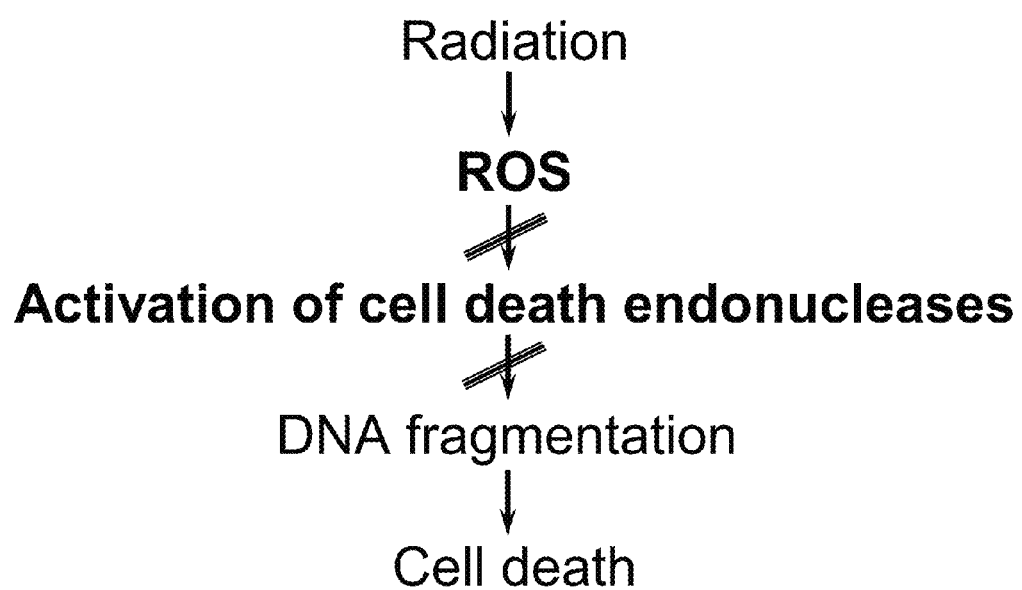
FIG. 2 illustrates a scheme of ROS and endonuclease-mediated cell death, and intersection points for cytoprotection.

The present invention provides compositions and methods for cytoprotection. It has been discovered that protection is provided by compositions that inhibit endonucleases that play a role in cell death. In particular, protection is provided by zinc chelates of aminothiols. These zinc chelates have dual cytoprotective effects. First, the $Zn^{2+}$ component directly inhibits nucleases. Second, the aminothiol component has antioxidant activity and indirectly inhibits nucleases by preventing nuclease induction and release (see FIG. 2). Furthermore, it was discovered that cytoprotection is provided even when the zinc chelate is administered after a cellular injury.

(I) Zinc Chelate Compounds a. Chemical and Physical Properties

One aspect of the invention provides a zinc chelate compound comprising at least one $Zn^{2+}$ ion and at least one aminothiol ligand. An aminothiol may be any chemical compound comprising an amine group and a thiol group. In one embodiment, the source of the aminothiol ligand is a compound comprising formula (I):

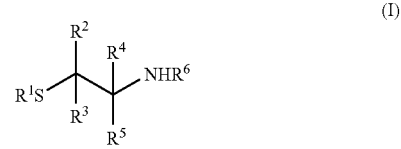

(I)

wherein:
$R^1$ is selected from the group consisting of hydrogen, phosphate, and acyl; and
$R^2$, $R^3$, $R^4$, $R^5$, and $R^6$ are independently selected from the group consisting of hydrogen, hydrocarbyl, and substituted hydrocarbyl.

In another embodiment, the compound comprises formula (I),
wherein:
$R^1$ is selected from the group consisting of hydrogen, phosphate, and acyl;
$R^2$ and $R^3$ are independently selected from the group consisting of hydrogen, alkyl, alkylamino, carboxyl, carboxylate ester, and carboxamide;
$R^4$ and $R^5$ are independently selected from the group consisting of hydrogen, alkyl, carboxyl, carboxylate ester, and carboxamide; and
$R^6$ is selected from the group consisting of hydrogen, alkyl, and acyl.

In an exemplary iteration of this embodiment, $R^1$, $R^2$, $R^3$, and $R^5$ are each hydrogen; $R^4$ is carboxyl; and $R^6$ is acetyl (see compound (Ia) in Table A.

Another aspect of the invention provides a zinc chelate compound comprising at least one $Zn^{2+}$ ion and at least one aminothiol ligand, wherein the source of the ligand is a compound comprising formula (II):

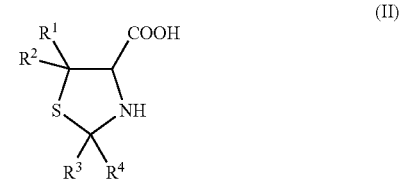

(II)

wherein:
$R^1$ and $R^2$ are independently selected from the group consisting of hydrogen, hydrocarbyl, and substituted hydrocarbyl, wherein $R^1$ and $R^2$ together may form a group selected from the group consisting of =O, =S, and a hydrocarbyl ring comprising from three to six members; and $R^3$ and $R^4$ are independently selected from the group consisting of hydrogen, hydrocarbyl, and substituted hydrocarbyl, wherein $R^3$ and $R^4$ together may form a group selected from the group consisting of =O, =S, and a hydrocarbyl ring comprising from three to six members.

In another embodiment, the compound comprises formula (II), wherein:

$R^1$ and $R^2$ are independently selected from the group consisting of hydrogen, alkyl, substituted alkyl, and alkenyl, wherein $R^1$ and $R^2$ together may form =O; and $R^3$ and $R^4$ are independently selected from the group consisting of hydrogen, alkyl, substituted alkyl, alkenyl, and a monoscaccharide derivative having the formula $(CHOH)_n CH_2OH$, wherein $R^3$ and $R^4$ together may form =O, and n is from 1 to 4.

In an exemplary iteration of this embodiment, $R^1$, $R^2$, $R^3$, and $R^4$ are each hydrogen (see compound (IIa) in Table A). In another exemplary iteration, $R^1$ and $R^2$ are both hydrogen, and $R^3$ and $R^4$ together form =O (see compound (IIb) in Table A). In yet another exemplary iteration, $R^1$, $R^2$, and $R^3$ are each hydrogen, and $R^4$ is propyl (see compound (IIc) in Table A). In a further exemplary iteration, $R^1$, $R^2$, and $R^3$ are each hydrogen, and $R^4$ is $(CHOH)_3CH_2OH$ (see compound (IId) in Table A).

TABLE A

Exemplary Compounds

| Compound | Structure |
|---|---|
| Ia | 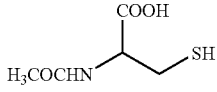 |
| IIa | 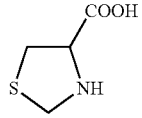 |
| IIb | 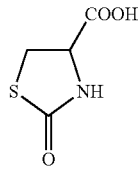 |
| IIc | 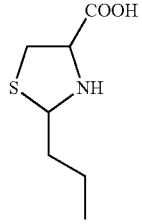 |
| IId | 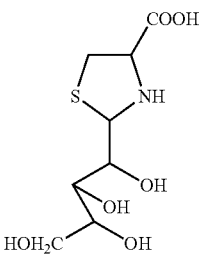 [SMILES: O=C(O)C1CSC(C(O)C(O)C(O)CO)N1] |

The ratio of aminothiol ligand to zinc ion in the chelate molecule may generally vary from 1:1 to 3:1 or higher. Typically, a zinc chelate may comprise a mixture of 1:1, 2:1, and 3:1 species. Preferably, the ratio of aminothiol ligand to zinc ion in the chelate molecule may generally vary from about 0.5:1 to about 2.5:1. In an aqueous medium, the relative proportions of these species are determined by the applicable stability constants. As will be appreciated by a skilled artisan, where the number of ligands equates to the charge on the zinc ion (and depending upon the ligand) the charge is typically balanced because the carboxyl moieties of the ligands are in deprotonated form. For example, in the chelate species wherein ligand to zinc ion ratio is 2:1, each of the hydroxyl or amino groups is understood to be bound by a coordinate covalent bond to the zinc ion, while an ionic bond prevails between each of the carboxylate groups and the zinc ion. Where the number of ligands exceeds the charge on the zinc ion, e.g., in a 3:1 chelate, the ligand residues in excess of the charge typically may remain in a protonated state to balance the charge.

In an exemplary embodiment, the ratio of aminothiol ligand to zinc ion in the chelate molecule may be about 1:1. For example, the ratio of ligand to zinc ion in compound (IIb) may be about 1:1. In another exemplary embodiment, the ratio of aminothiol ligand to zinc ion in the chelate molecule may be about 2:1. For example, the ratio of ligand to zinc ion in compounds (Ia) and (IId) may be about 2:1.

The zinc chelates of the present invention may be prepared using procedures known to those of skill in the art, as detailed in Example 3. A zinc chelate compound typically will have a UV/vis spectrum that differs from the spectrum of the ligand. Aminothiol ligands tend to have two absorption maxima, which occur around 205 nm and 230 nm. The two absorption maxima of zinc chelates of aminothiols, however, tend to occur around 210 nm and 225 nm. Thus, the first absorption peak of a chelate is shifted to a longer wavelength relative to its ligand, and the second absorption peak of a zinc chelate is shifted to a shorter wavelength relative to its ligand.

It is contemplated that, if appropriate, one or more of the compounds forming the zinc chelates of the present invention can exist in tautomeric, geometric or stereoisomeric forms without departing from the scope of the invention. The present invention contemplates all such compounds, including cis- and trans-geometric isomers, E- and Z-geometric isomers, R- and S-enantiomers, diastereomers, D-isomers, L-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

b. Functional Properties

The zinc chelate compounds of the invention typically have dual cytoprotection activities. First, the zinc component of the chelate may have the ability to directly inhibit nucleases. Second, the aminothiol component of the chelate may have antioxidant activity, whereby it has the ability to inhibit the induction and release of nucleases (in response to ROS).

Generally speaking, endonucleases play a causative role in cell death. Table B lists the known cell death endonucleases. Except for the cation-independent DNase II, all of the known cell death endonucleases, which represent about 90-95% of the endonuclease activity in a cell, are $Ca^{2+}/Mg^{2+}$-dependent, $Mg^{2+}$-dependent, or $Mn^{2+}$-dependent. Furthermore, all of the known cell death endonucleases are inhibited by $Zn^{2+}$.

TABLE B

Cell Death Endonucleases

| Name | Cations | Inhibitors* |
|---|---|---|
| DNase I | $Ca^{2+}/Mg^{2+}$, $Ca^{2+}/Mn^{2+}$ | $Zn^{2+}$, G-actin, EDTA |
| DNase X | $Ca^{2+}/Mg^{2+}$ | $Zn^{2+}$, EDTA |
| DNase 1L2 | $Ca^{2+}/Mg^{2+}$ | $Zn^{2+}$, ATA |
| DNase gamma | $Ca^{2+}/Mg^{2+}$ | $Zn^{2+}$, ATA, EDTA |
| DNase II | — | $Zn^{2+}$, $Cu^{2+}$ |
| CAD**/DFF40 | $Mg^{2+}$ | $Zn^{2+}$, ICAD/DFF45 |
| EndoG | $Mn^{2+}$ | $Zn^{2+}$ |

*ATA, aurintricarboxylic acid, EDTA, ethylenediaminetetraacetic acid
**CAD, caspase-activated DNase Endonucleases are enzymes that cleave one or more phosphodiester bonds within a nucleic acid. The nucleic acid is typically a deoxynucleic acid (DNA). The nucleic acid may be a double-stranded or single-stranded. The cleaved polynucleotide or oligonucleotide typically has a phosphate group at the 5' end and a hydroxyl group at the 3' end.

In one embodiment, the zinc chelate compound may inhibit DNase I. In a majority of cells, DNase I is the most abundant endonuclease. DNase I generally is present in all tissues in all species examined. Human DNase I may be found, for example, as GenBank Accession No. AAA63170. In another embodiment, the zinc chelate compound may inhibit DNase gamma. Human DNase gamma, which is DNase I family member, may be found, for example, as GenBank Accession No. AAC23652. In still another embodiment, the zinc chelate compound may inhibit DNase X, another DNase I family member. Human DNase X may be found, for example, as GenBank Accession No. NP_001009933. In yet another embodiment, the zinc chelate compound may inhibit DNase 1 L2, which is also a DNase I family member. Human DNase 1 L2 may be found, for example, as GenBank Accession No. AAH35205. In an alternate embodiment, the zinc chelate compound may inhibit DNase II. Human DNase 11 may be found, for example, as GenBank Accession No. 000115. In another alternate embodiment, the zinc chelate compound may inhibit CAD. Human CAD may be found, for example, as GenBank Accession No. 076075. In still another embodiment, the zinc chelate compound may inhibit EndoG. EndoG is the second most abundant endonuclease and is present in a majority of cells in all species examined. Human EndoG may be found, for example, as GenBank Accession No. NP_004426.

Figure 1:
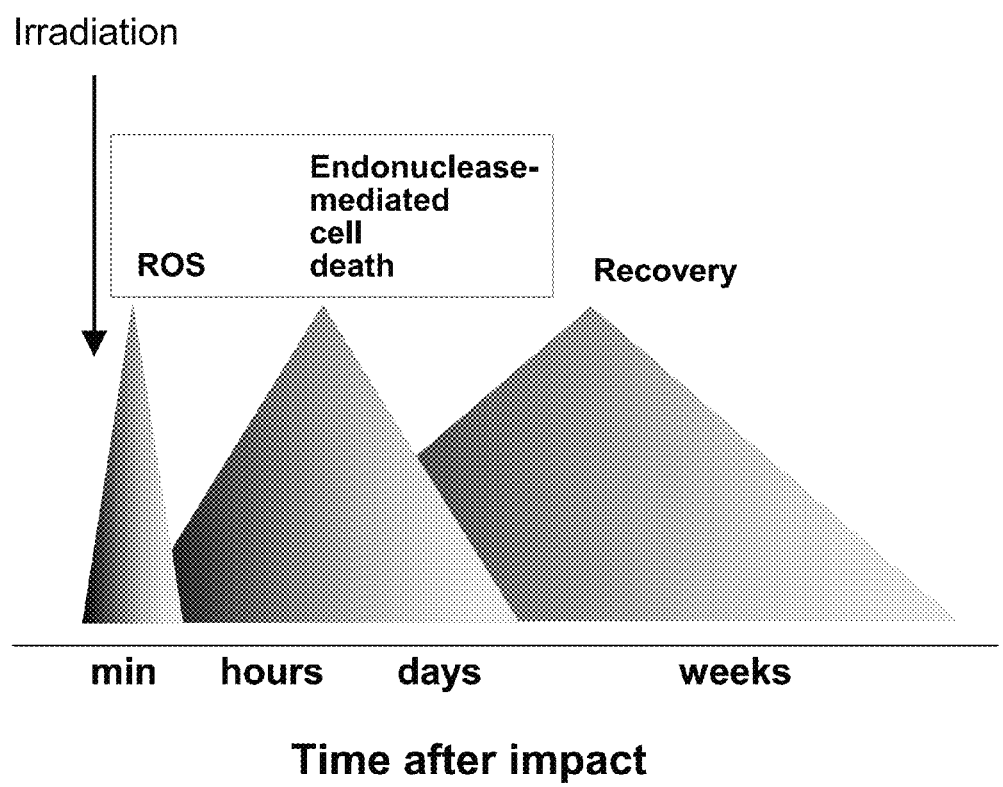
FIG. 1 illustrates an approximate timeline of cellular events following cellular injury by irradiation.

The aminothiol component of the zinc chelate may possess antioxidant activity. In particular, it may react with oxidants, such as ROS, and counteracts their effects. For example, ROS may activate endonucleases by inducing their synthesis and release from cellular compartments, thereby allowing nuclear import of endonucleases. Alternatively, ROS may directly activated endonucleases via the direct oxidation of the molecule. DNA damage induced by endonucleases is generally several orders of magnitude greater than the direct damage by ROS. The peak of endonucleases activity usually follows oxidative stress by several hours, induces apoptotic cell death, and then declines in a few days (see FIG. 1).

(II) Methods for Protecting a Cell from a Cellular Injury

A further aspect of the invention encompasses methods for protecting a cell from a cellular injury. The method comprises contacting the cell with a composition comprising a nuclease inhibitor and an antioxidant.

a. Cellular Injury

The cellular injury may be any cellular injury or assault that leads to increased levels of ROS. In one embodiment, the cellular injury may be a radiation-induced cell injury, i.e., an injury due to exposure to ionizing radiation. The radiation may be gamma radiation, beta radiation, X-ray radiation, or ultraviolet radiation. The ultraviolet radiation may be UVA, UVB, UVC, or deep UV (DUV) (e.g., as used in laser technology). The dose of the radiation may range from background radiation to more than 50 Gy. In one embodiment, the dose of the radiation may range from background radiation to about 5 Gy. In another embodiment, the dose of the radiation may range from about 5 Gy to about 20 Gy. In yet another embodiment, dose of the radiation may range from about 20 Gy to at least about 50 Gy.

In an alternate embodiment, the cellular injury may be a chemically-induced injury. The chemical may be a chemotherapeutic agent. Suitable chemotherapeutic agents include alkylating agents, such as cisplatin, carboplatin, oxaliplatin, mechlorethamine, cyclophosphamide, chlorambucil, and the like; anti-metabolites, such as azathioprine, 6-mercaptopurine, cytosine arabinoside (Ara-C), methotrexate, and so forth; anti-tumor antibiotics, such as actinomycin, adriamycin, bleomycins, dactinomycin, daunorubicin, mitomycins, and the like; and anti-cytoskeletal agents, such as colchicines, taxanes, vinblastine, vincristine, vindesine, and so forth. In another embodiment, the chemical may be an antibiotic. Suitable antibiotics include aminoglycosides (such as, e.g., gentamicin), carbapenems, cephalosporins, penicillins, sulfonamides, tetracyclines, and the like. In still another embodiment, the chemical may be an analgesic agent. Suitable analgesic agents include acetaminophen, non-steroidal anti-inflammatory agents (such as salicylates, profens (i.e., ibuprofen, naproxen, etc.), COX-2 inhibitors, and so forth), and narcotics. In another embodiment, the chemical may be an alcohol or a recreational drug. In an alternate embodiment, the chemical may be an herbicide (such as, e.g., a glyphosphate, an EPSPS inhibitor, an ALS inhibitor, etc.) or a pesticide (such as, e.g., an organophosphate, an organochlorine, etc.). In an alternate embodiment, the chemical may be produced by a microorganism, such as E. coli endotoxin, sepsis-inducing toxins, and the like.

In yet another embodiment, the cellular injury may be an ischemia-reperfusion injury. The ischemia-reperfusion injury may lead to organ failure. Examples of organ failure include myocardial infarction, heart failure, kidney failure, liver failure, multiple organ failure, and the like.

In an alternate embodiment, the cellular injury may be a thermal injury. The thermal injury may be due to exposure to an elevated temperature. The thermal injury may also be due accidental and therapeutic laser exposure. Alternatively, the thermal injury may be due exposure to extremely low temperatures.

In a further embodiment, the cellular injury may be a mechanical trauma. Mechanical trauma is an injury to any portion of the body from a blow, crush, cut, or penetrating wound. The complications of mechanical trauma are usually related to fracture, hemorrhage, and infection. For example, the mechanical trauma may be a crush injury that leads to muscle damage or rhabdomyolysis.

b. Cell

The type of cell can and will vary depending upon, among other things, the type of cellular injury. Non-limiting examples of suitable cells include cardiac stromal cells, cardiac endothelium, lung stromal cells, lung endothelium, kidney stromal cells, kidney endothelium, intestinal crypt cells, intestinal villi, intestinal stromal cells, intestinal endothelium, spleen white pulp cells, spleen red pulp cells, thyroid stromal cells, thyroid endothelium, pancreatic stromal cells, pancreatic endothelium, bone marrow, white blood cells, bladder cells, ovary cells, and prostate cells.

In some embodiments, the cell may be disposed in a subject. Suitable subjects include humans and animals. Suitable animals include companion animals such as cats, dogs, gerbils, and the like; research animals such as a mice, rats, rabbits, etc.; agricultural animals such as cows, pigs, horses, goats, sheep, poultry, and so forth; zoo animals; and primates such as a chimpanzee, a monkey, or a gorilla. In exemplary embodiments, the subject is a human.

c. Composition

The composition comprises a nuclease inhibitor and an antioxidant. In general, the composition will protect the cell from cellular damage. The cellular damage may range from minimal damage, such as oxidation of molecules in the cell, to severe damage (i.e., cell death).

i. nuclease inhibitor. In general, the nuclease inhibitor will be a cell death endonuclease inhibitor. Cell death endonucleases are detailed above. Preferably, the cell death endonuclease inhibitor will be zinc ions, as detailed above. The zinc may complex with an anion and form a salt. The anion may be inorganic or organic. Suitable inorganic anions include acetate, hydrochloride, nitrate, sulfate, and so forth. Suitable organic anions include aspartate, citrate, glucoheptonate, gluconate, glycerate, methionine, picolinate, and the like. The zinc may complex with a ligand and form a chelate. Non-limiting examples of suitable ligands include amino acids, dipeptides, polypeptides, salicylates, carboxylates, aminothiols, and so forth.

ii. antioxidant. The antioxidant of the composition may be an aminothiol. Suitable aminothiols include compounds comprising formula (I) or formula (II), as detailed above. In particular, the aminothiol may be N-acetylcysteine, captopril, cysteamine, cysteine, N-(2-mercaptopropionyl)glycine, penicillamine, 2-oxothiazolidine-4-carboxylic acid, 2-n-propylthiazolidine-4-carboxylic acid, 2-(1-ribosyl)thiazolidine-4-carboxylic acid, or thiazolidine-4-carboxylic acid. In a preferred embodiment, the zinc chelating antioxidant may be N-acetylcysteine, captopril, penicillamine, 2-n-propylthiazolidine-4-carboxylic acid, or 2-(1-ribosyl)thiazolidine-4-carboxylic acid.

In another embodiment, the composition may comprise a zinc chelate. A zinc chelate comprises at least one zinc ion and at least one ligand. The ligand may be a compound comprising formula (I) or formula (II), as detailed above. In preferred embodiment, the ligand may be N-acetylcysteine, captopril, cysteamine, cysteine, 3,5-diisopropylsalicylic acid, N-(2-mercaptopropionyl)glycine, penicillamine, 2-oxothiazolidine-4-carboxylic acid, 2-n-propylthiazolidine-4-carboxylic acid, 2-(1-ribosyl)thiazolidine-4-carboxylic acid, or thiazolidine-4-carboxylic acid. In preferred embodiment, the zinc chelating antioxidant may be N-acetylcysteine, captopril, penicillamine, 2-n-propylthiazolidine-4-carboxylic acid, or and 2-(1-ribosyl)thiazolidine-4-carboxylic acid.

iii. dosage forms. The compositions detailed herein may be manufactured in one or several dosage forms. Suitable dosage forms include a tablet, including a suspension tablet, a chewable tablet, an effervescent tablet or caplet; a pill; a powder such as a sterile packaged powder, a dispensable powder, and an effervescent powder; a capsule including both soft or hard gelatin capsules such as HPMC capsules; a lozenge; a sachet; a sprinkle; a reconstitutable powder or shake; a troche; pellets; granules; liquids; suspensions; emulsions; or semisolids and gels. Alternatively, the pharmaceutical compositions may be incorporated into a food product or powder for mixing with a liquid, or administered orally after only mixing with a non-foodstuff liquid. The compositions, in addition to being suitable for administration in multiple dosage forms, may also be administered with various dosage regimens, as detailed below.

The dosage form may include an excipient. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agent.

In one embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 Daltons.

In another embodiment, the excipient may be a filler. Suitable fillers include carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as a-tocopherol or ascorbate, and antimicrobials, such as parabens, chlorobutanol or phenol.

In another embodiment, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Suitable flavors may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The exipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials.

In various embodiments, the excipient may include a pH modifier. In certain embodiments, the pH modifier may include sodium carbonate or sodium bicarbonate. In other embodiments, an antioxidant such as BHT or BHA is utilized.

The weight fraction of the excipient or combination of excipients in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The particle size of the ingredients forming the composition may be an important factor that can effect bioavailability, blend uniformity, segregation, and flow properties. In general, smaller particle sizes of a compound increases the bioabsorption rate of the compound with substantially poor water solubility by increasing the surface area. The particle size of the compounds and excipients can also affect the suspension properties of the formulation. For example, smaller particles are less likely to settle and therefore form better suspensions. In various embodiments, the average particle size of the dry powder of the various ingredients (which can be administered directly, as a powder for suspension, or used in a solid dosage form) is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In some applications the use of particles less than 15 microns in diameter may be advantageous. In these cases colloidal or nano-sized particles in the particle size range of 15 microns down to 10 nanometers may be advantageously employed.

The compositions of the present invention may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation, and the like.

The compositions of the invention also may be manufactured into one or several dosage forms and formulated for the controlled, sustained or timed release of one or more of the ingredients. In this context, typically one or more of the ingredients forming the composition is microencapsulated or dry coated prior to being formulated into the dosage form. By varying the amount and type of coating and its thickness, the timing and location of release of a given ingredient or several ingredients (in either the same dosage form, such as a multi-layered capsule, or different dosage forms) may be varied.

The coating can and will vary depending upon a variety of factors, including, the particular ingredient, and the purpose to be achieved by its encapsulation (e.g., flavor masking, maintenance of structural integrity, or formulation for time release). The coating material may be a biopolymer, a semi-synthetic polymer, or a mixture thereof. The microcapsule may comprise one coating layer or many coating layers, of which the layers may be of the same material or different materials. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. The coating material may also comprise a mixture of biopolymers. As an example, the coating material may comprise a mixture of a polysaccharide and a fat.

In an exemplary embodiment, the coating may be an enteric coating. The enteric coating generally will provide for controlled release of the ingredient, such that release of an active ingredient may be accomplished at some generally predictable location in the lower intestinal tract below the point at which release would occur without the enteric coating. In certain embodiments, multiple enteric coatings may be utilized.

The enteric coating is typically, although not necessarily, a polymeric material that is pH sensitive. A variety of anionic polymers exhibiting a pH-dependent solubility profile may be suitably used as an enteric coating in the practice of the present invention to achieve delivery of the active ingredients to the lower gastrointestinal tract. Suitable enteric coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (i.e., purified lac). Combinations of different coating materials may also be used to coat a single capsule.

The thickness of a microcapsule coating may be an important factor in some instances. For example, the "coating weight," or relative amount of coating material per dosage form, generally dictates the time interval between oral ingestion and drug release. As such, a coating utilized for time release of the ingredient or combination of ingredients into the gastrointestinal tract is typically applied to a sufficient thickness such that the entire coating does not dissolve in the gastrointestinal fluids at pH below about 5, but does dissolve at pH about 5 and above. The thickness of the coating is generally optimized to achieve release of the ingredient at approximately the desired time and location.

As will be appreciated by a skilled artisan, the encapsulation or coating method can and will vary depending upon the ingredients used to form the composition and coating, and the desired physical characteristics of the microcapsules themselves. Additionally, more than one encapsulation method may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995).

d. Contact Between the Cell and the Composition i. timing of contact. The timing of contact between the cell and the composition can and will vary depending upon the embodiment. The cell may be contacted with the composition before the cellular injury, after the cellular injury, or a combination thereof. For example, the cell may be contacted with the composition before the cellular injury, e.g., from about three days to about five minutes before the cellular injury. In one embodiment, the cell may be contacted with the composition from about three days to about one day before the cellular injury. In another embodiment, the cell may be contacted with the composition from about 24 hours to about four hours before the cellular injury. In still another embodiment, the cell may be contacted with the composition from about four hours to about five minutes before the cellular injury. In a preferred embodiment, the cell may be contacted with the composition from about 1.0 hour to about 0.5 hour before the cellular injury. Alternatively, the cell may be contacted with the composition from about five minutes after the cellular injury to about seven days after the cellular injury. In one embodiment, the cell may be contacted with the composition from about five minutes to about 24 hours after the cellular injury. In another embodiment, the cell may be contacted with the composition from about one day to about three days after the cellular injury. In still another embodiment, the cell may be contacted with the composition from about three days to about seven days after the cellular injury. Furthermore, the cell may be contacted with the composition both before the cellular injury and after the cellular injury, as detailed above. In a preferred embodiment, the cell may be contacted with the composition from about 5 minutes after the cellular injury to about 1 day after the cellular injury.

ii. route of administration. Typically, the composition agent will be administered to a subject orally, but other routes of administration may also be used. Additional routes of administration include inhalation, transdermal, transmucosal, intravenous, intramuscular, and subcutaneous.

Preparations for oral administration were detailed above in the section on dosage forms. For example, oral preparations may be enclosed in gelatin capsules or compressed into tablets. Oral preparations may also be administered as aqueous suspensions, elixirs, or syrups.

For parenteral administration (including subcutaneous, intradermal, intravenous, intramuscular, and intraperitoneal), the preparation may an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

iii. doses. The amount of agent that is administered to the subject and the duration of the treatment can and will vary depending upon the type of cellular injury, the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

As an example, the composition may be administered orally before and after exposure to an ionizing radiation. In an iteration of this embodiment, the composition may be administered from about 0.5 to about 1 hour before exposure to the radiation, and at a dose that ranges from about 0.01 to about 2.5 gram. The composition then may be administered every 4 to 6 hours for about 7 days after exposure to the radiation, and at a dose that ranges from about 0.01 to about 2 g. Preferably, the dose administered before exposure to the radiation may be about 0.5 g and the dose administered for about 7 days after the radiation may be about 0.25 g. Alternatively, the composition may be administered orally only after exposure to the ionizing radiation. In an iteration of this embodiment, the composition may be administered every 4 to 6 hours for about 7 days after exposure to the radiation, and at a dose that ranges from about 0.01 to about 2 g. Preferably, the composition may be administered for about 7 days after exposure, and at a dose of about 0.25 g.

iv. optional coadministration agents. The composition may be coadministered with at least one agent that substantially protects the Zn-chelate from being effected by gastric acid. In one embodiment, the agent may be a buffering agent. The buffering agent will generally be an antacid. Suitable antacids include those comprised of alkali metal (a Group IA metal including, but not limited to, lithium, sodium, potassium, rubidium, cesium, and francium) or alkaline earth metal (Group IIA metal including, but not limited to, beryllium, magnesium, calcium, strontium, barium, radium) carbonates, phosphates, bicarbonates, citrates, borates, acetates, phthalates, tartrate, succinates and the like, such as sodium or potassium phosphate, citrate, borate, acetate, bicarbonate and carbonate. In another embodiment, the agent may be a proton pump inhibitor. Proton pump inhibitors are typically acid labile pharmaceutical agents that substantially inhibit $H^+/K^+$ ATPase. In one embodiment, the proton pump inhibitor may be a substituted bicyclic aryl-imidazole, wherein the aryl group may be, e.g., a pyridine, a phenyl, or a pyrimidine group and is attached to the 4- and 5-positions of the imidazole ring. Proton pump inhibitors comprising a substituted bicyclic aryl-imidazoles include, but are not limited to, omeprazole, hydroxyomeprazole, esomeprazole, lansoprazole, pantoprazole, rabeprazole, dontoprazole, habeprazole, perprazole, tenatoprazole, ransoprazole, pariprazole, leminoprazole. In still another embodiment, the agent may be a histamine H2-receptor antagonist, commonly known as an H2 blocker. H2-blockers generally inhibit secretion of acid by the parietal cells in the stomach lining, and thereby, cause gastric acid pH to increase. Suitable H2 blockers include cimetidine (commercially available as Tagamet or Tagamet HB); ranitidine (commercially available as Zantac); famotidine (commercially available as Pepcid AC or Pepcid); ebrotidine; pabutidine; lafutidine; and nizatidine (commercially available as Axid AR or Axid).

(III) Methods for Radioprotection of a Cell.

A further aspect of the invention provides a method for radioprotection of a cell. The method comprises contacting the cell that is subject to an ionizing radiation with a zinc chelate of an aminothiol, wherein the zinc chelate has endonuclease inhibitor activity and antioxidant activity.

Zinc chelates of aminothiol that may provide radioprotection include zinc-N-acetylcysteine (Zn-NAC), zinc-captopril, zinc-penicillamine, zinc-2-oxothiazolidine-4-carboxylic acid (Zn-OTCA), zinc-2-n-propylthiazolidine-4-carboxylic acid (Zn-PTCA), zinc-2-(1-ribosyl)thiazolidine-4-carboxylic acid (Zn-RibCys), and zinc-thiazolidine-4-carboxylic acid (Zn-TCA), as detailed above in section (I). In a preferred embodiment, the zinc chelate may be Zn-NAC, Zn-RibCys, Zn-penicillamine, Zn-captopril, or Zn-PTCA. Examples of ionizing radiation, subjects, routes of administration, timing of administration, and doses of zinc chelate are detailed above in section (II).

Definitions

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R_1$, $R_1O-$, $R_1R_2N-$, or $R_1S-$, $R_1$ is hydrocarbyl, heterosubstituted hydrocarbyl, or heterocyclo, and $R_2$ is hydrogen, hydrocarbyl or substituted hydrocarbyl.

The term "alkyl" as used herein describes groups that are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups that are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "cytoprotection," as used herein, refers to the act of protecting a cell as "protecting" is defined below.

The term "heteroatom" shall mean atoms other than carbon and hydrogen.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting," as used herein, refers to preventing, reducing, or reversing the cellular damage associated with a radiation, chemical, thermal, ischemia-reperfusion, or mechanical injury to a cell. In particular, it refers to preventing or reducing cell death. The term "protection" as used herein, refers to the act of protecting as "protecting" is defined immediately above.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Role of Endonucleases in Radiation Induced Apoptosis

Female CD-1 mice (n=4) were irradiated with an 8 Gy dose and apoptotic endonuclease-mediated DNA fragmentation was measured in different organs 40 hours after irradiation. For this, tissue sections were subjected to terminal deoxynucleotidyl transferase mediated dUTP nick end labeling (TUNEL) staining with the In Situ Cell Death Detection Kit from Roche Diagnostics (Indianapolis, Ind.). After washing and counterstaining with 4,6-diamidino-2-phenylindole (DAPI) sections were mounted under coverslips using the Antifade kit (Molecular Probes; Eugene, Oreg.) and analyzed under an Axioskop-2 mot plus microscope (Carl Zeiss, Göttingen Germany) with green filter set #31001, red filter set #11010v2 and blue filter set #31000 from Chroma Technology Corp. (Rockingham, Vt.). Images and acquisitions were performed using digital camera AxioCam MRm (Carl Zeiss) and software Axiovision 3.1 (Carl Zeiss).

Statistical comparisons of the data were carried out using SPSS software (SPSS Inc., Chicago, Ill.). The simple Student's t-test was used for comparison of two sets of data. For comparison of several experimental data sets with a single control, the Bonferoni's modification of t-test was used along with the one-way ANOVA followed by post-hoc tests. For the comparison of data that would require multivariate comparison, the two-way ANOVA/MANOVA was applied. A $P<0.05$ was considered significant.

As shown in Table 1, the irradiation induced marked DNA fragmentation in a variety of different organs. Organs with prominent DNA fragmentation included intestine, bone marrow, and spleen.

TABLE 1

Radiosensitivity of Mouse Tissues.

| Organ | Structure | Sensitivity to irradiation* |
|---|---|---|
| Heart | Myocardium | − |
| | Endocardium | − |
| | Stromal tissue/endothelium | ± |
| Lung | Pulmonary alveoli | − |
| | Stromal tissue/endothelium | ± |
| Liver | Hepatic lobules | − |
| | Intra/extrahepatic ducts | − |
| | Stromal tissue/endothelium | − |
| Kidney | Gloms | − |
| | Tubules and ducts | − |
| | Stromal tissue/endothelium | + |
| Intestine | Crypts | ± |
| | Villii | ++ |
| | Stromal tissue/endothelium | + |
| Spleen | White pulp | ++ |
| | Red pulp | ± |
| Thyroid | Follicles | − |
| | Stromal tissue/endothelium | ± |
| Salivary glands | Glandular alveoli | − |
| | Stromal tissue/endothelium | − |
| Pancreas | Pancreatic acini | − |
| | Ducts | − |
| | Islets | − |
| | Stromal tissue/endothelium | ± |
| Skeletal muscle | | − |
| Bone Marrow | | ++ |
| White blood cells | | ± |

*"−", no difference from non-irradiated tissue; "±", some damage caused by irradiation; "+", significant damage caused by irradiation; "++", very significant damage caused by irradiation.

To determine whether genetic inactivation of DNase I could provide protection to some organs, DNase I knock-out (KO) mice were also irradiated. DNase I KO mice (CD-1 background) were generated by Dr. H. Mannherz's group at the University of Bochum, Germany (Napirei et al., 2000, Nature Genet. 25(2):177-181). The mice were bred as heterozygotes that were genotyped by PCR. DNase I KO and wild type mice (n=4 per group) were irradiated and analyzed as described above.

Figure 3:
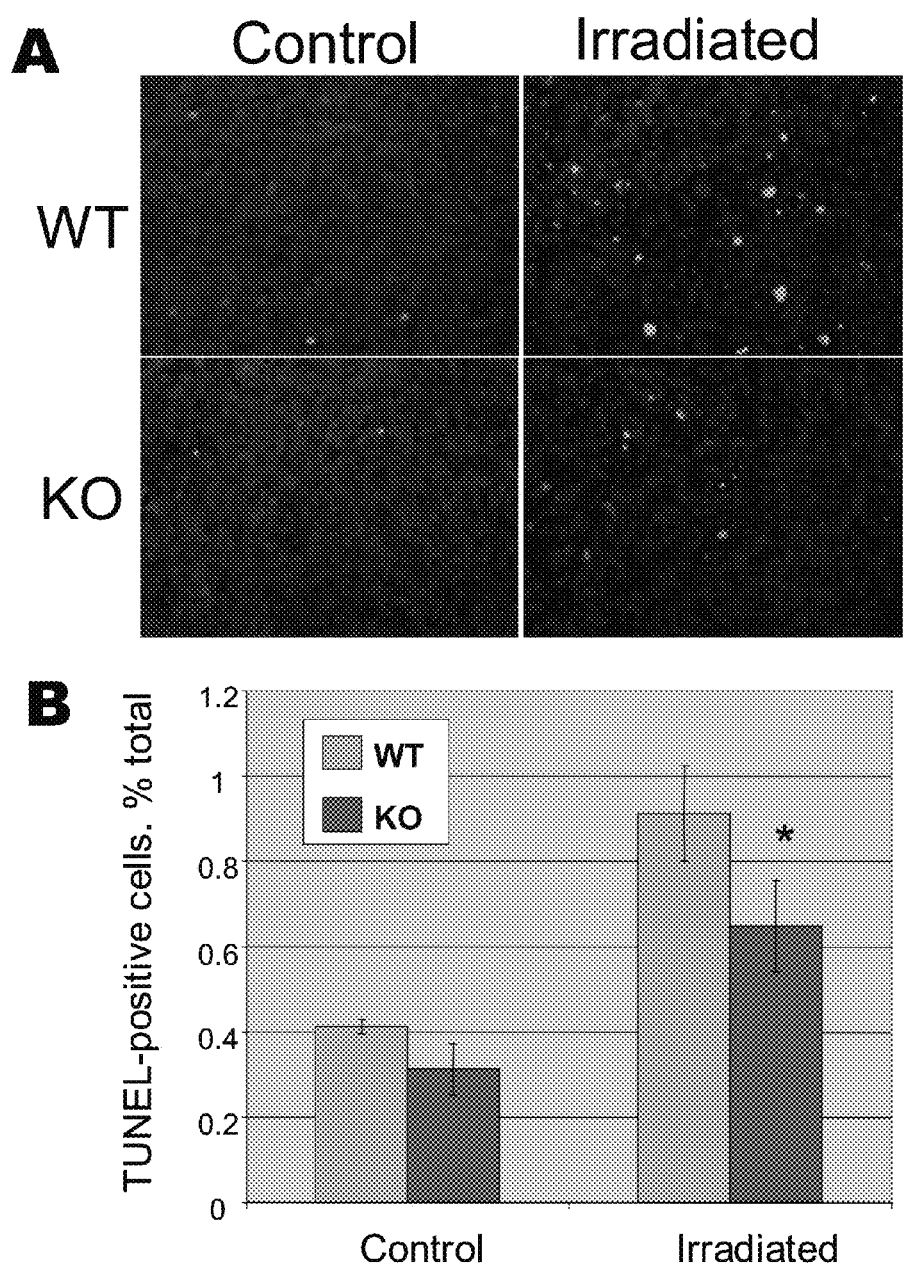
FIG. 3 illustrates an increase of apoptotic DNA fragmentation measured by TUNEL assay in mouse spleen (white pulp) of knock-out (KO) and wild type (WT) mice 40 hours after irradiation with 8 Gy ($LD_{50/30}$). (A) Presents representative micrograph images, with TUNEL-positive staining in green. (B) Presents a plot of the percent of TUNEL-positive cells in each group. N=4 per group, *p<0.05 compared to wild type.

Some, but not all organs of the knock-out mice were protected against the harmful effects of radiation. The most protection was observed in the white pulp of the spleen (FIG. 3) and the intestine, indicating that DNase I mediated the radiation-induced DNA fragmentation in these two organs.

Example 2

Zinc Chelates Inhibit DNase I Activity In Vitro

Figure 4:
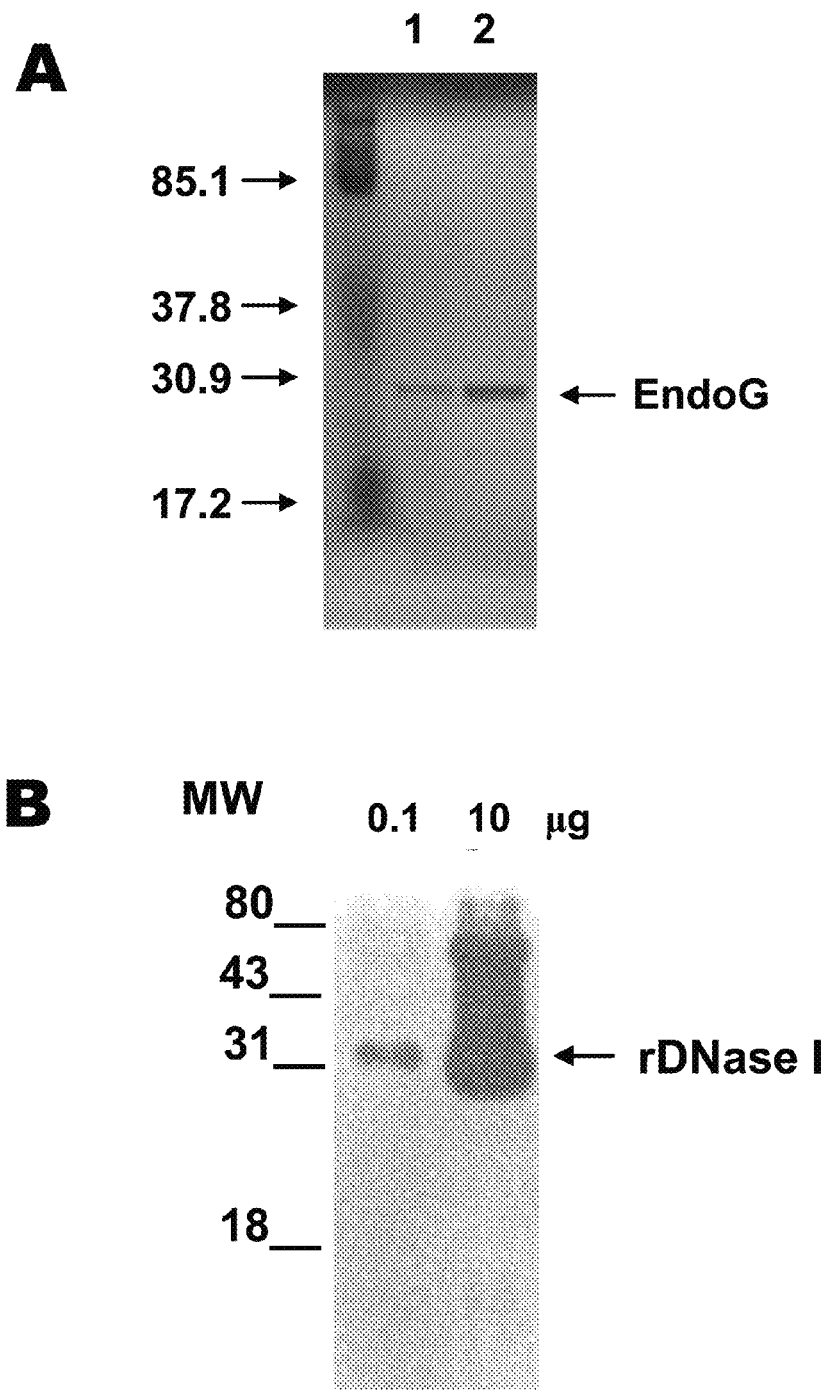
FIG. 4 illustrates zymogram gel electrophoresis of recombinant nucleases. (A) Presents recombinant EndoG. The 29 kDa endonuclease activity band is indicated by the arrow to the right. Lane 1 is human EndoG and lane 2 is mouse EndoG. (B) Presents recombinant DNase I. The 34 kDa endonuclease activity band is indicted by arrow to the right. The 70 kDa dimer is visible in the gel after overloading (10 µg protein/well).

It was hypothesized that $Zn^{2+}$-chelates of aminothiols could provide radioprotection via their direct inhibition of nucleases and their antioxidant properties (i.e., prevent nuclease induction and release). To test this hypothesis, the activity of Zn(II) chelates to inhibit nucleases was assayed in vitro. For this, DNase I and EndoG were cloned, recombinant nuclease were expressed and purified for the in vitro assay. Human and mouse mature EndoG cDNA was reverse transcribed by RT-PCR from either normal human breast epithelial HMEC cells (Clonetics, Walkersville, Md.) or immortalized mouse proximal tubule epithelial TKPTS cells (obtained from D. Elsa Bello-Reuss, University of Texas Medical Branch, Galveston). The plasmid for mature human EndoG (A49-K297) with a C-terminal histidine tag and mouse mature EndoG (A45-K294) with a C-terminal histidine tag were constructed by inserting coding cDNA into pET29b(+) (Novagen, San Diego, Calif.) and expressed in *Escherichia coli* BL21 (DE3) cells using standard procedures. Expression of the recombinant proteins was induced by IPTG. The expressed recombinant protein was purified by HisTrap FF crude Kit (GE Healthcare, Uppsala, Sweden) and stored in 20 mM Tris-HCl, ph 7.5, 0.5 M NaCl, 2 mM 2-mercaptoethanol, and 50% glycerol. The recombinant EndoG was assayed by Western blotting (data not shown) or SDS/PAGE zymography (FIG. 4A). Recombinant DNase I was produced using a similar approach (FIG. 4B).

Endonuclease activity was measured using a plasmid incision assay. Activity was measured in 20 μl samples containing 1 μg pBR322 plasmid DNA, 10 mM Tris-HCl, pH 7.7, 25 μg/ml bovine serum albumin V fraction, 0.5 mM dithiothreitol, 5 mM $MgCl_2$, 2 mM $CaCl_2$, and 2 μl endonuclease. After 1 hour incubation at 37° C., the reaction was stopped by the addition 5 μl 1% SDS, 100 mM EDTA. Digested DNA was then subjected to a 1% agarose gel electrophoresis at 7 V/cm for 1 hour at room temperature. The gel was stained in 0.5 μg/ml ethidium bromide solution for 20 minutes and photographed under fluorescent light. Scanning densitometer Fotodyne (Fotodyne Inc., Hartland, Wis.) was utilized to quantify the relative amount of endonuclease-treated plasmid DNA present in a covalently closed circular DNA (cccDNA), open circular DNA (ocDNA) or linear DNA (linDNA). One endonuclease unit was defined as the amount of enzyme required to convert 1 μg cccDNA to ocDNA and linDNA.

Figure 5:
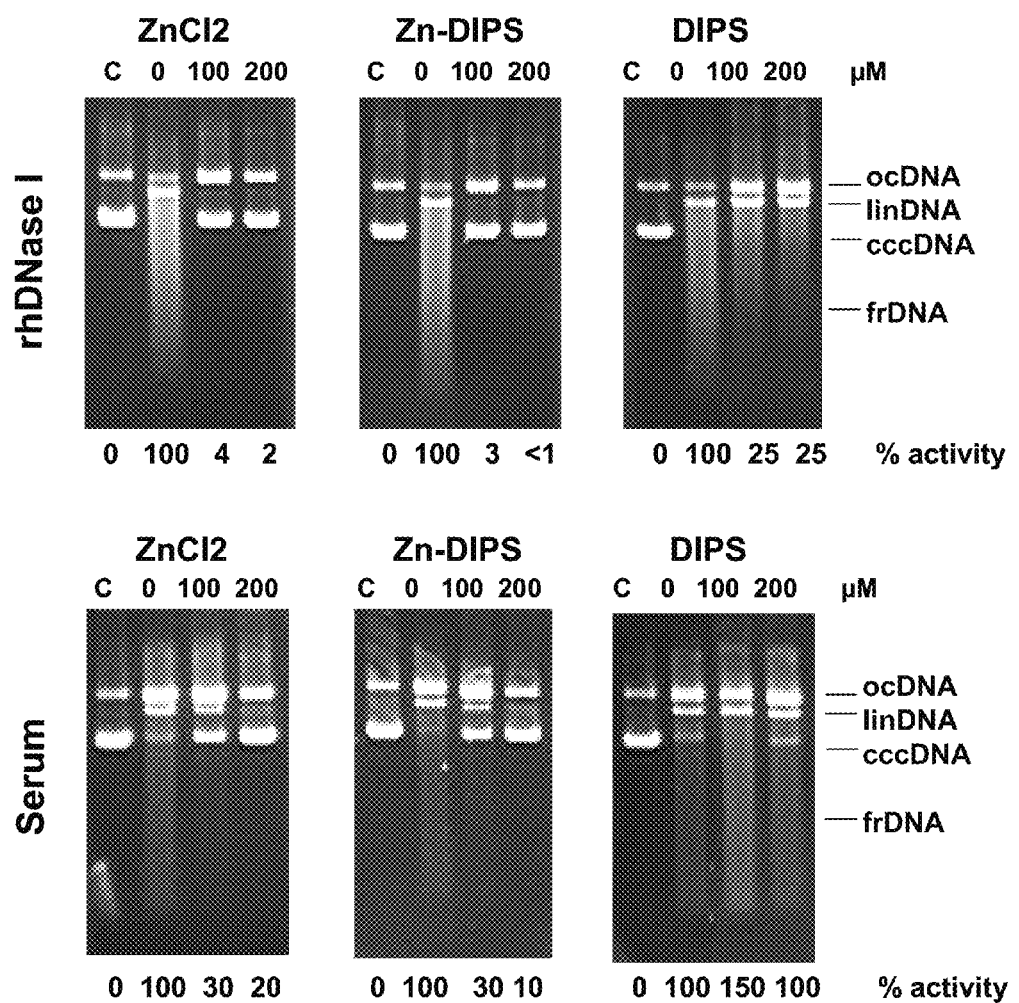
FIG. 5 illustrates inhibition of recombinant human DNase I (rhDNase 1) or rat serum DNase (Serum) by $ZnCl_2$ and Zn-DIPS (0, 100 or 200 µM). "C" indicates control non-digested pBR322 plasmid DNA. Circular covalently closed DNA (cccDNA) is converted first to open circular DNA (ocDNA), then to linear DNA (linDNA) and finally to fragmented (frDAN). Endonuclease activity is shown as percentage of 0 µM samples.

Recombinant DNase I and rat serum DNase (which is predominantly rat DNase I) were incubated with 0, 100, or 200 μM of a $Zn^{2+}$-chelate (i.e., Zn-3,5-diisopropylsalicylic acid (DIPS), Zn-gluconate, or Zn-glycinate), a ligand (i.e., DIPS, gluconic acid, or glycine, as negative controls), or $ZnCl_2$ (as positive control). All $Zn^{2+}$-chelates inhibited DNase I and serum DNase activity, whereas the ligands alone showed no effect. The best inhibition was achieved by using Zn-DIPS (FIG. 5). Recombinant EndoG had a similar pattern of inhibition (data not shown).

Example 3

Synthesis of $Zn^{2+}$-Chelates

Several ligands (some of which are diagrammed in Table 2) were used to generate $Zn^{2+}$-chelates (see Table 3).

TABLE 2

Ligands for Zinc Chelates.

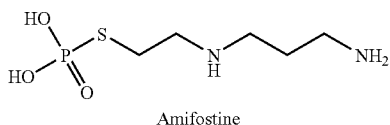

Amifostine

TABLE 2-continued

Ligands for Zinc Chelates.

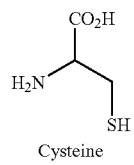

Cysteine

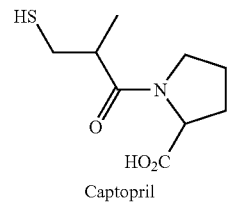

Captopril

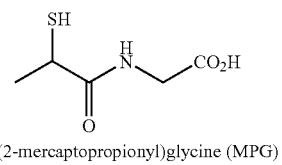

N-(2-mercaptopropionyl)glycine (MPG)

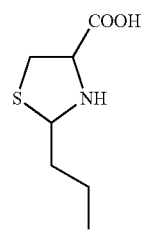

2-propylthiazolidine-4-carboxylic acid (PTCA)

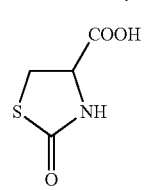

2-oxothiazolidine-4-carboxylic acid (OTCA)

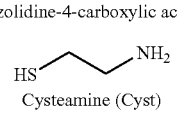

Cysteamine (Cyst)

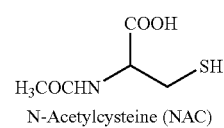

N-Acetylcysteine (NAC)

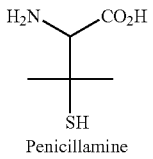

Penicillamine

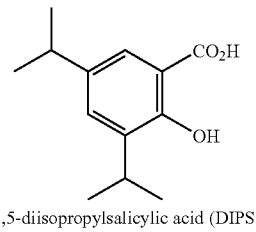

3,5-diisopropylsalicylic acid (DIPS)

TABLE 2-continued

Ligands for Zinc Chelates.

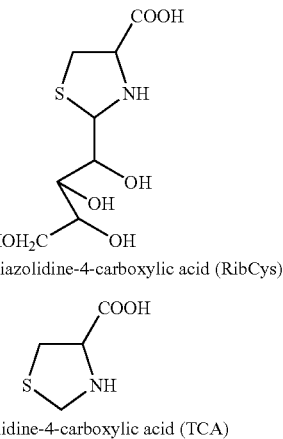

2-(1-ribosyl)thiazolidine-4-carboxylic acid (RibCys)

Thiazolidine-4-carboxylic acid (TCA)

TABLE 3

Compounds Tested for Radiosensitivity

| Ligand (chelator) | $Zn^{2+}$-chelate |
|---|---|
| Amifostine | — |
| — | Zn-chloride |
| 3,5-Diisoproylsalicylic acid (DIPS) | Zn-DIPS |
| Gluconic acid | Zn-Gluconate |
| Glycine | Zn-Glycinate |
| Cysteine (Cys) | Zn-Cys |
| N-Acetylcysteine (NAC) | Zn-NAC |
| Cysteamine (CYST) | Zn-Cyst |
| N-(2-Mercaptopropionyl)glycine (MPG) | Zn-MPG |
| Thiazolidine-4-carboxylic acid (TCA) | Zn-TCA |
| Penicillamine | Zn-Penicillamine |
| Captopril | Zn-Captopril |
| 2-(1-Ribosyl)thiazolidine-4-carboxylic acid (RibCys) | Zn-RibCys |
| 2-propylthiazolidine-4-carboxylic acid (PTCA) | Zn-PTCA |
| 2-oxothiazolidine-4-carboxylic acid (OTCA) | Zn-OTCA |

Cysteine (cat # C6852), N-acetylcysteine (cat #A9165), N-2-mercaptopropionyglycine (MPG) (cat # M6635), penicillamine (cat # P4875), captopril (cat # C4042), thiazolidine-4-carboxylic acid (TCA) (cat # T0631), 2-oxo-thiazolidine-4-carboxylic acid (OCTA) (cat # O-6254), and other chemicals were purchased from Sigma-Aldrich Company (St. Louis, Mo.). Amifostine was made available by researchers at the National Cancer Institute. The thiazolidines, 2-n-propylthiazolidine-4-carboxylic acid (PTCA) and 2-(1-ribosyl)thiazolidine-4-carboxylic acid (RibCys) were synthesized using methods according to Nagasawa et al., 1984 (J Med Chem 27:591-596) and Robers et al. (1991 Med Chem Res 1:213-219). The $Zn^{2+}$-chelates were synthesized using one of the following methods.

Method 1. This method was used to produce a $Zn^{2+}$-chelate from the hydrochloride salt of a ligand. $Zn^{2+}$-chelates of this type were synthesized by stirring a 2:1:2 molar ratio of aqueous aminothiol, $ZnCl_2$, and NaOH at room temperature for several hours, followed by filtration of precipitate and purification by recrystallization. For example, the $Zn^{2+}$-chelate of cysteamine was produced by this method.

Method 2. This method was used to produce a $Zn^{2+}$-chelate from the water-soluble, free base form of a ligand. A 2:1 molar ratio of ligand and zinc acetate was stirred for several hours in aqueous solution at room temperature. The precipitated chelate was filtered, washed with cold water, and recrystallized from the appropriate solvent mixture. The $Zn^{2+}$-chelates of cysteine and penicillamine were prepared using this method.

Method 3. This method was used to produce a $Zn^{2+}$-chelate from the ethanol-soluble, free base form of a ligand. Separate solutions containing the appropriate molar rations of zinc acetate and ligand were prepared in warm ethanol. The zinc acetate solution was added to the ligand solution in 2.0 mL portions while stirring. The mixture was allowed to cool to room temperature and then refrigerated overnight. The precipitated $Zn^{2+}$-chelate was filtered, washed with cold ethanol, and recrystallized from the appropriate solvent mixture. $Zn^{2+}$-chelates of N-acetylcysteine, 2-mercaptopropionylglcine, captopril, and the 2-substituted thiazolidine-4-carboxylic acid derivatives were prepared by this method.

After synthesis, mass spectra and UV/visible, FTIR, and NMR spectra of each compound were recorded. Molecular formulas of the $Zn^{2+}$-chelates were determined by elemental analysis (e.g., see Tables 4 and 5). The $Zn^{2+}$-chelates may be represented by the general formula $Zn_xL_y(H_2O)_z$. Elemental analyses of the chelates were obtained from Micro-Analysis, Inc., Wilmington, Del. All of the chelates were high melting solids that decomposed above 200° C. Most had limited water solubility, but were sufficiently soluble to permit biological testing. One exception was the chelate formed from N-acetylcysteine. It was very water soluble and had moderate ethanol solubility.

TABLE 4

Molecular Formulas* of Zinc Chelates

| Chelate | X | Y | Z | Molecular Formula |
|---|---|---|---|---|
| Zn-Cysteine | 1 | 2 | 2 | $C_6H_{12}N_2O_4S_2Zn \cdot 2H_2O$ |
| Zn-Cysteamine | 1 | 2 | 0 | $C_4H_{12}N_2S_2Zn$ |
| Zn-MPG | 2 | 2 | 1 | $C_8H_{16}N_2S_2O_6Zn_2H_2O$ |
| Zn-NAC | 2 | 2 | 1 | $C_{10}H_{16}N_2O_6S_2Zn_2 \cdot H_2O$ |
| Zn-Penicillamine | 2 | 2 | 0.5 | $C_{10}H_{20}N_2O_4S_2Zn_2 \cdot 0.5 H_2O$ |
| Zn-Captopril | 1 | 1 | 0.5 | $C_9H_{13}NO_3SZn \cdot 0.5 H_2O$ |
| Zn-RibCys | 1 | 2 | 0 | $C_{16}H_{28}N_2O_{12}S_2Zn_2$ |

*$Zn_xL_y(H_2O)_z$

TABLE 5

Elemental Analysis Data

| Compound | % C expected | % H expected | % N expected | % C found | % H found | % N found |
|---|---|---|---|---|---|---|
| Zn-Cysteine | 21.09 | 4.72 | 8.20 | 21.15 | 4.18 | 7.85 |
| Zn-Cysteamine | 22.07 | 5.55 | 12.49 | 22.04 | 5.11 | 12.86 |
| Zn-MPG | 25.46 | 3.39 | 5.94 | 25.71 | 3.50 | 5.84 |
| Zn-NAC | 26.50 | 3.09 | 6.18 | 26.59 | 3.10 | 5.98 |
| Zn-Penicillamine | 27.53 | 4.82 | 6.42 | 27.67 | 4.53 | 6.21 |
| Zn-Captopril | 37.32 | 4.48 | 4.83 | 37.48 | 4.45 | 4.66 |
| Zn-RibCys | 33.72 | 4.91 | 4.91 | 33.32 | 4.92 | 4.68 |

The UV/vis spectra of the chelates were distinguishable from those of the ligands. Aminothiols tend to have two absorption maxima ($\lambda_{max}$), which occur around 205 nm and 230 nm. In the chelates, however, these absorption maxima occurred around 210 nm and 225 nm, respectively. In all cases, except for the chelate formed from captopril, the first absorption peak occurred at a noticeably longer wavelength, and the second absorption peak occurred at a noticeably shorter wavelength than its ligand.

Example 4

Antioxidant Activity of the $Zn^{2+}$-Chelates

Figure 6:
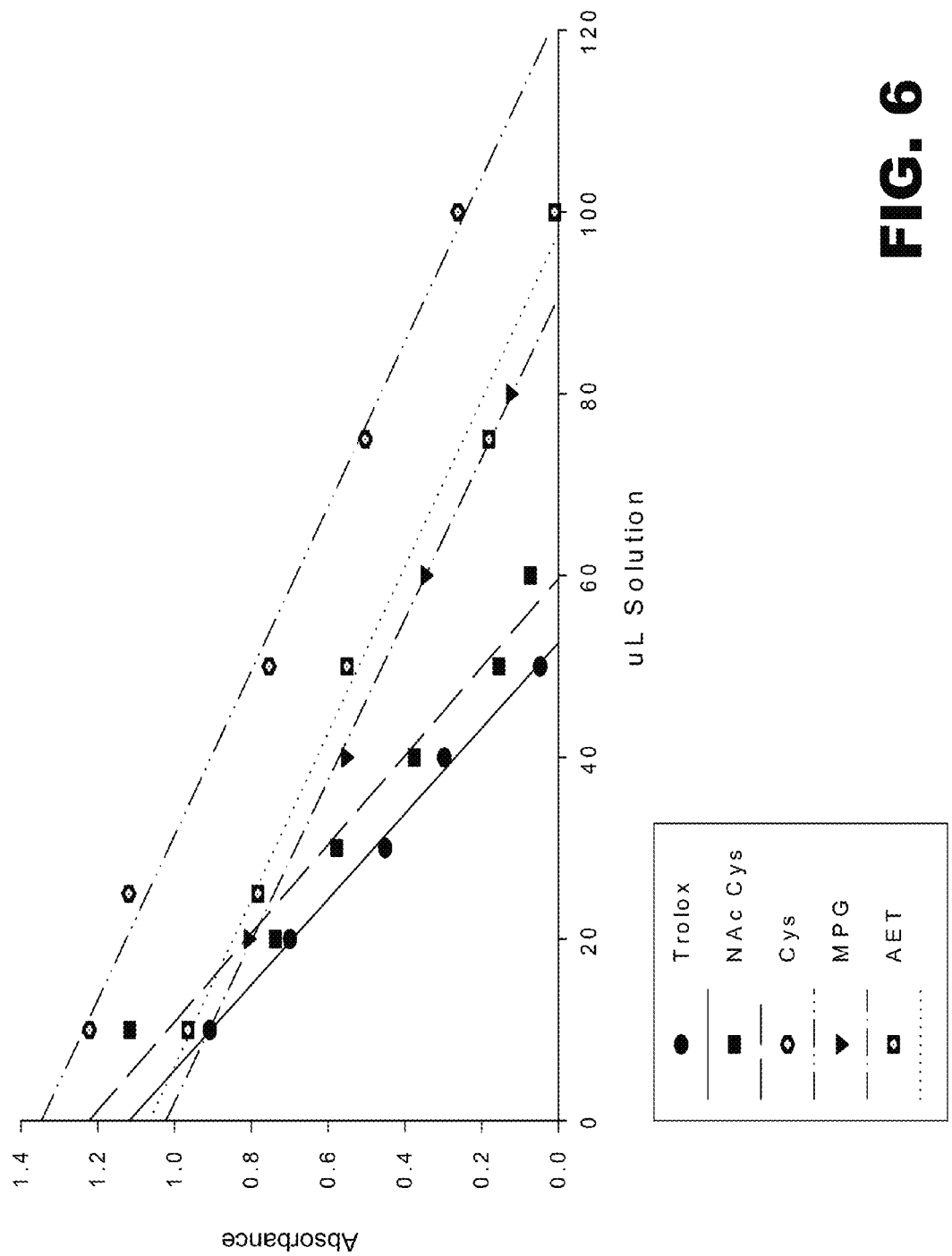
FIG. 6 illustrates Trolox Equivalent Antioxidant Capacity (TEAC) data for various aminothiol ligands.

The antioxidant capacity of the zinc chelates was measured using the 6-hydroxy-2,5,7,8-tetramethylchroman-2-carboxylic acid (Trolox)-Equivalent Antioxidant Capacity (TEAC) Assay (Randox Laboratories Ltd., Antrim, United Kingdom). FIG. 6 presents a graph of absorbance versus concentration for several of the ligands, from which antioxidant capacity was calculated. Antioxidant capacity was measured relative to the Trolox standard, which was assigned a TEAC value of 1.00. Table 6 shows the relative antioxidant capacities of the ligands and their zinc chelates. For all compounds, except for captopril, the chelate had a higher antioxidant capacity than the ligand. Penicillamine and its chelate were the strongest antioxidants. Unchelated $Zn^{2+}$ had no activity in this assay.

TABLE 6

TEAD Values of Ligands and Chelates.

| Compounds | Ligand | Chelate |
|---|---|---|
| Cysteine | 0.43 | 0.65 |
| Cysteamine | 0.40 | 0.87 |
| MPG | 0.53 | 0.97 |
| NAC | 0.88 | 1.73 |
| Penicillamine | 1.54 | 2.05 |
| Captopril | 0.90 | 0.90 |

Example 5

$Zn^{2+}$-Chelates Provide Radioprotection In Vitro

To determine the radioprotective effects of $Zn^{2+}$-chelates, U937 human promonocytic cells (ATCC number CRL-1593.2) were irradiated with or without $Zn^{2+}$-chelates added to the cells before or after irradiation, and radiation-induced cell death was measured 24 hr later using a propidium iodide (PI) assay. Propidium iodide was added to the cells at a final concentration of 4 µM and incubated for 15 minutes. Fluorescence (which indicates dead cells) was measured at 530/645 nm, and fluorescence was measured again after cell lysis with Triton-100 (1%, v/v) for 20 minutes (to give an estimate of total cells). The background (no cells) was subtracted, and the percent of the radiation-induced cell death was computed.

Figure 7A:
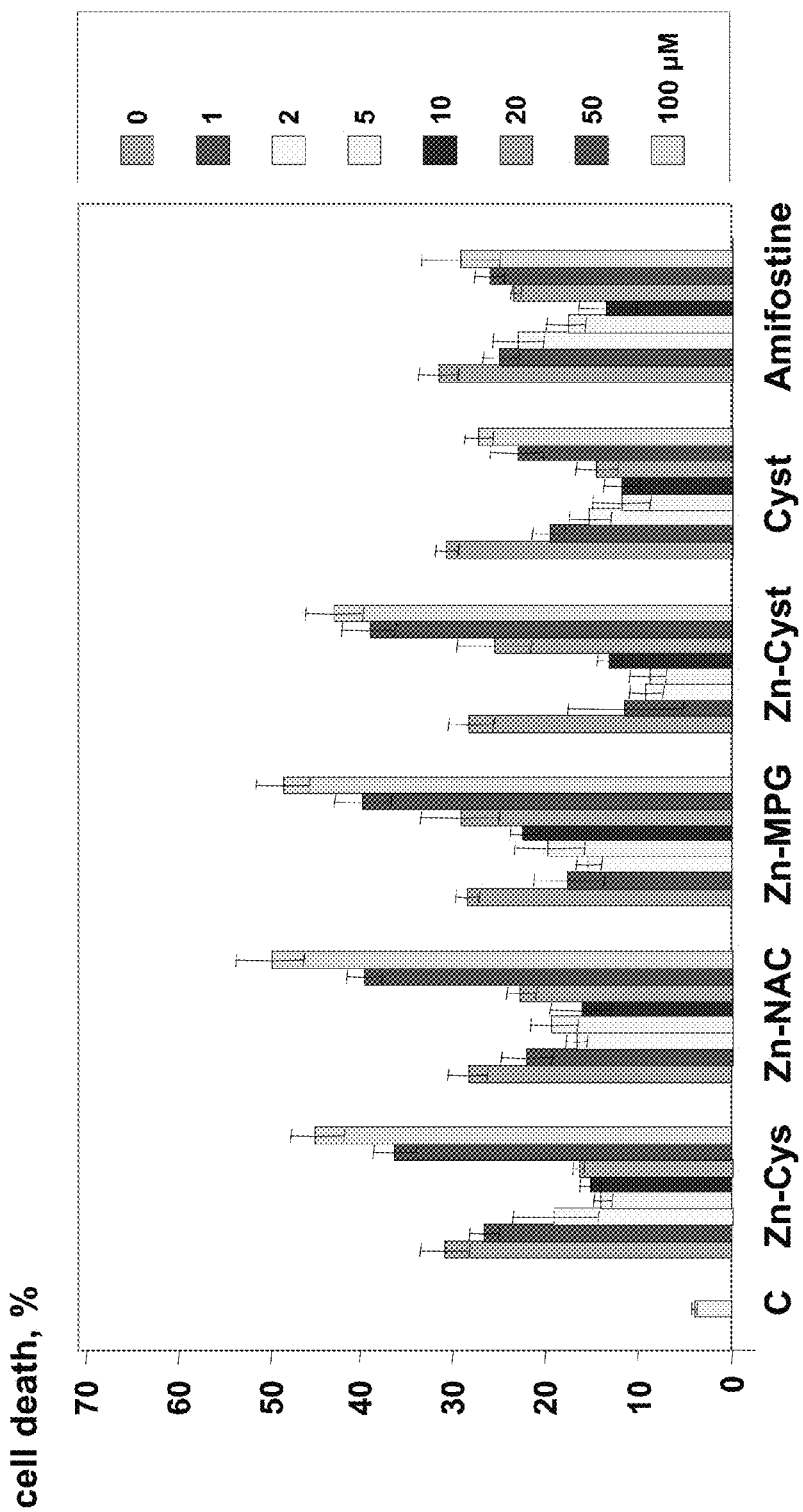
FIG. 7 illustrates radioprotection of U937 cells by $Zn^{2+}$-chelates. Cells were exposed to 50 Gy and cell death was measured 24 hours later using a propidium iodide assay. (A) Plots the percent of cell death when the chelates were added before irradiation. (B) Plots the percent of cell death when the chelates were added after irradiation. Zn-Cys ($Zn^{2+}$-Cysteine): Zn-NAC ($Zn^{2+}$-N-acetylcysteine); Zn-MPG ($Zn^{2+}$-N-(2-Mercapto-propionyglycine); Zn-Cyst ($Zn^{2+}$-Cysteamine). Cysteamine (Cyst) and Amifostine were used as positive controls.

Different concentrations (0-100 µM) of a compound were added to the cells, which were then irradiated with 50 Gy. The compounds tested were amifostine (positive control), cysteamine, Zn-cysteamine, Zn-N-(2-mercaptopropionyl)glycine (Zn-MPG), Zn-NAC, and Zn-cysteine. As shown in FIG. 7A, irradiation induced significant cell death, but cell death was inhibited if cells were irradiated in the presence of a $Zn^{2+}$-chelate (1-20 µM). The inhibition was similar or better (e.g., see Zn-cysteamine) than that induced by cysteamine or amifostine. Similar radioprotection by $Zn^{2+}$-chelates was also observed when a lactate dehydrogenase (LDH) release assay was used instead of the PI assay (data not shown). Furthermore, $Zn^{2+}$-chelates protected better than $ZnCl_2$ or ligand added separately or together with $ZnCl_2$.

Figure 7B:
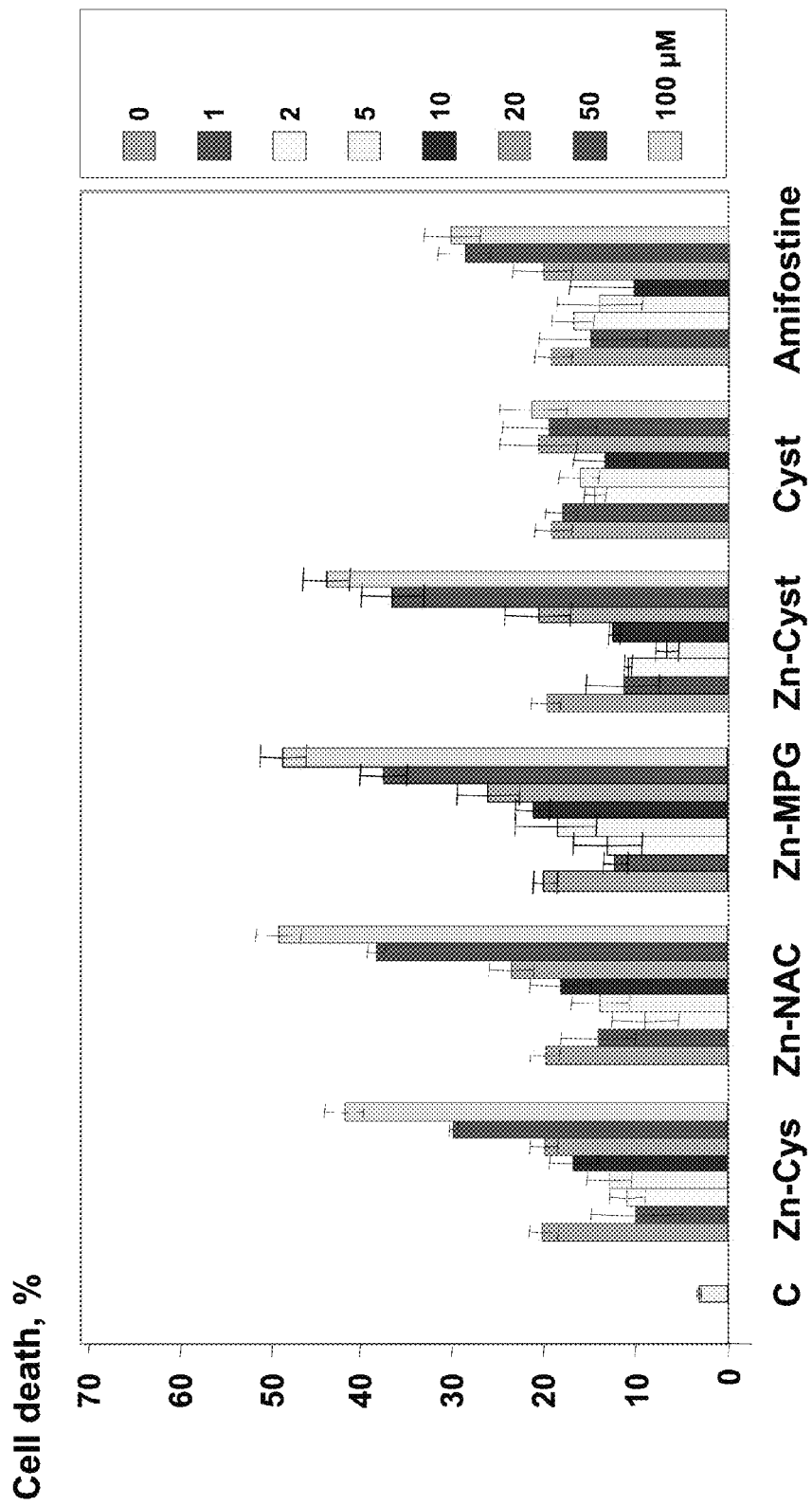

The $Zn^{2+}$-chelates provided radioprotection even if they were added after irradiation (FIG. 7B). In fact, the concentrations of the $Zn^{2+}$-chelates needed to provide cytoprotection after irradiation, however, were lower than those required when the chelates were added prior to irradiation.

Figure 8:
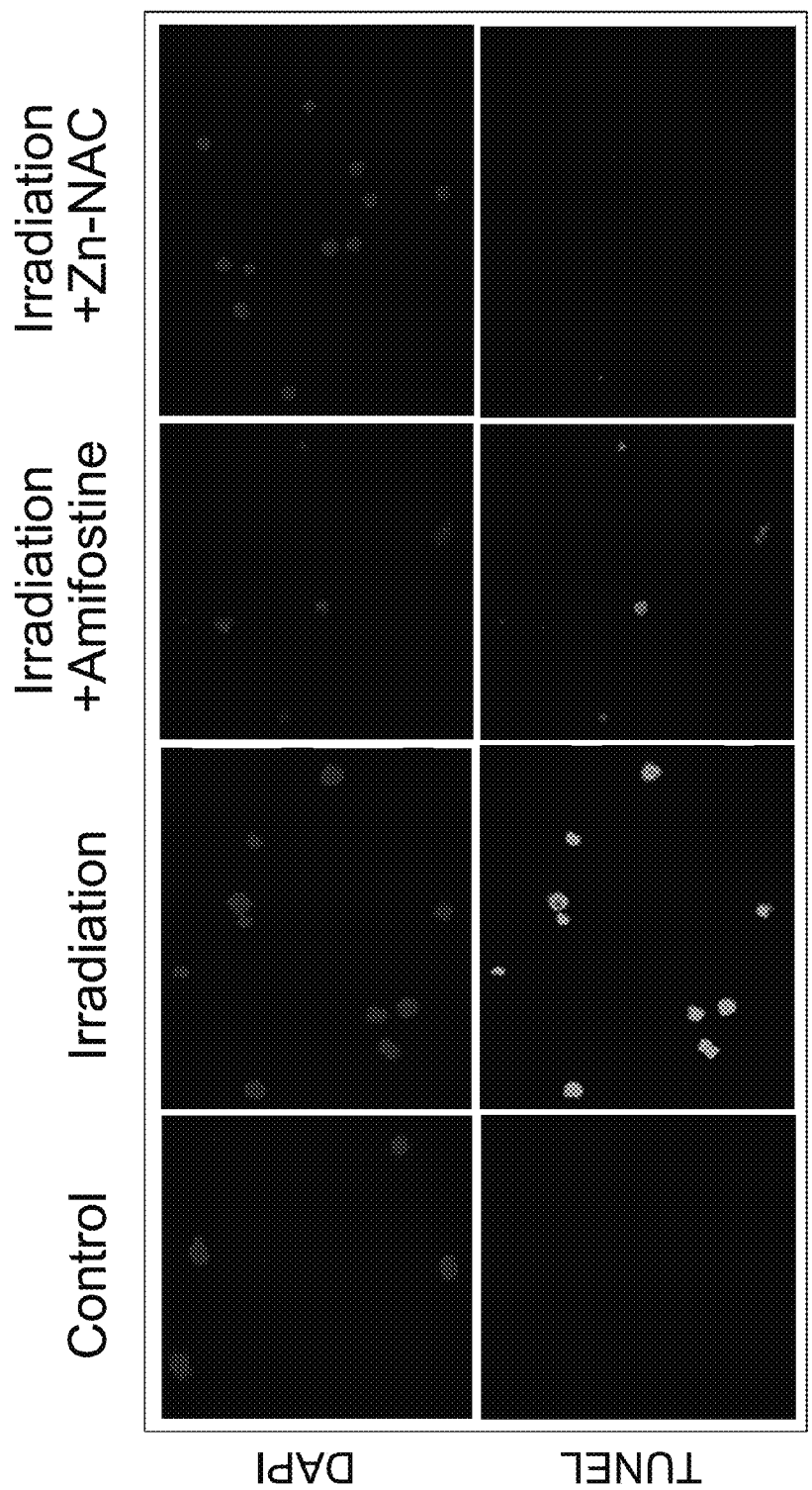
FIG. 8 illustrates inhibition of DNA fragmentation and cell death of U937 cells by $Zn^{2+}$-N-acetylcysteine (Zn-NAC) added before irradiation (50 Gy). DNA fragmentation and cell death were measured 24 hours later by TUNEL assay with nuclear DNA counterstained by DAPI. Amifostine was used as positive control of radioprotection.

The ability of the $Zn^{2+}$-chelates to inhibit radiation-induced DNA fragmentation was also examined. U937 cells were exposed to amifostine (as a positive control) or $Zn^{2+}$-N-acetylcysteine (Zn-NAC), irradiated as described above, and DNA fragmentation and cell death were measured 24 hr later using a TUNEL assay, essentially as described in Example 1. It was found that irradiation did induce DNA fragmentation in these cells, and the DNA fragmentation was inhibited by either of the compounds (FIG. 8).

Example 6

$Zn^{2+}$-Chelates Provide Cytoprotection From Lower Radiation Doses

Considering that the $LD_{50/30}$ (i.e., the dose that induces radiation syndrome in 50% of the animals at 30 days) for mice is approximately 8 Gy (Bichay et al., 1986, Strahlenther Onkol, 162(6):391-399), the 50 Gy dose used to irradiate the cells in the previous example was rather high. Thus, the $Zn^{2+}$-chelates were tested for radioprotection against a more physiological dose of radiation. The $Zn^{2+}$-chelates tested were Zn-NAC, Zn-captopril, Zn-2-propylthiazolidine-4-carboxylic acid (Zn-PTCA), and Zn-penacillamine. U937 cells were exposed to a $Zn^{2+}$-chelate (10 µM), irradiated with 4 Gy, and DNA fragmentation and apoptosis were measured using a single-cell gel electrophoresis assay (also know as Comet assay) 24 hr after irradiation. Alkaline or neutral Comet assays were performed using CometAssay™ kits from Trevigen (Gaithersburg, MC) according to the manufacture's instructions. The slides were analyzed under an epifluorescense microscope using the Comet assay image analysis software (CometScore; TriTek, Sumerduck, Va.).

Figure 9A:
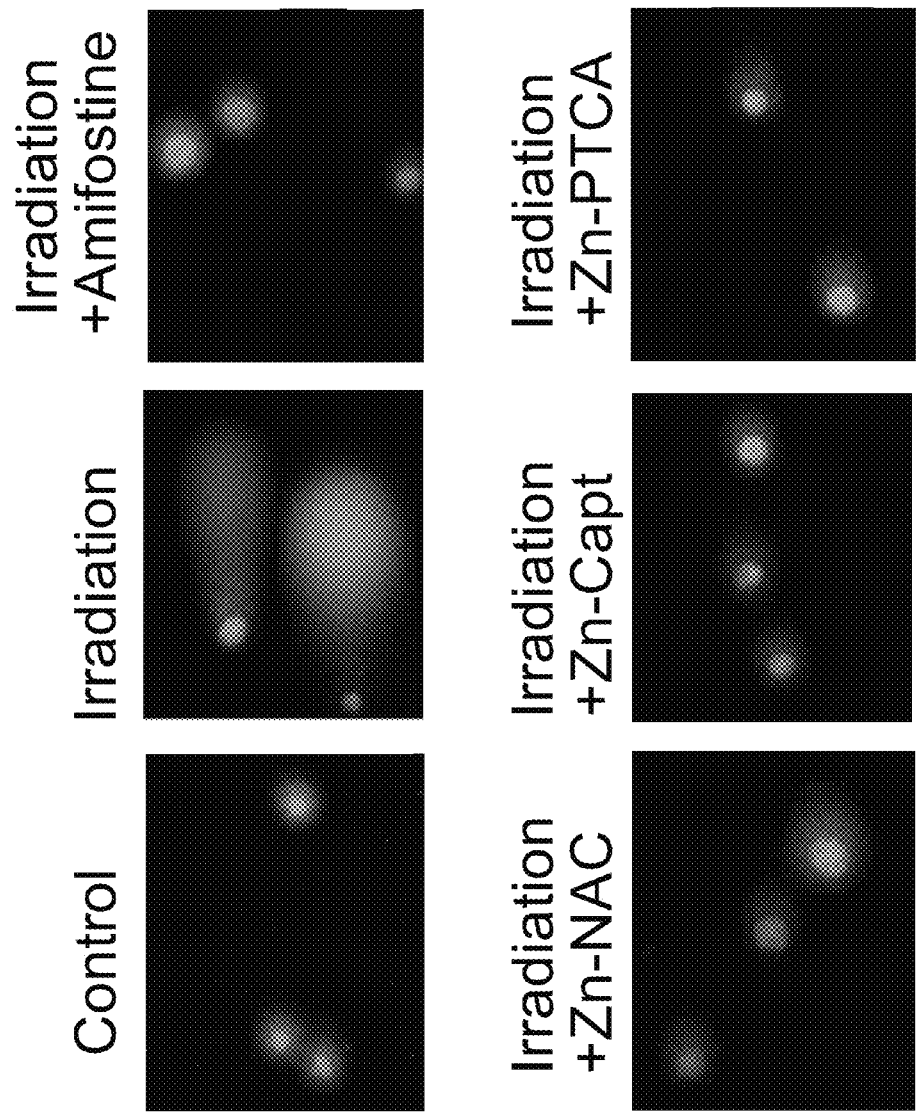
FIG. 9 illustrates radioprotection of U937 cells by $Zn^{2+}$-chelates (10 µM) added before irradiation (4 Gy) as measured using an alkaline Comet assay 24 hours after irradiation. (A) Presents representative micrograph images. (B) Presents the Comet scores.
Figure 9B:
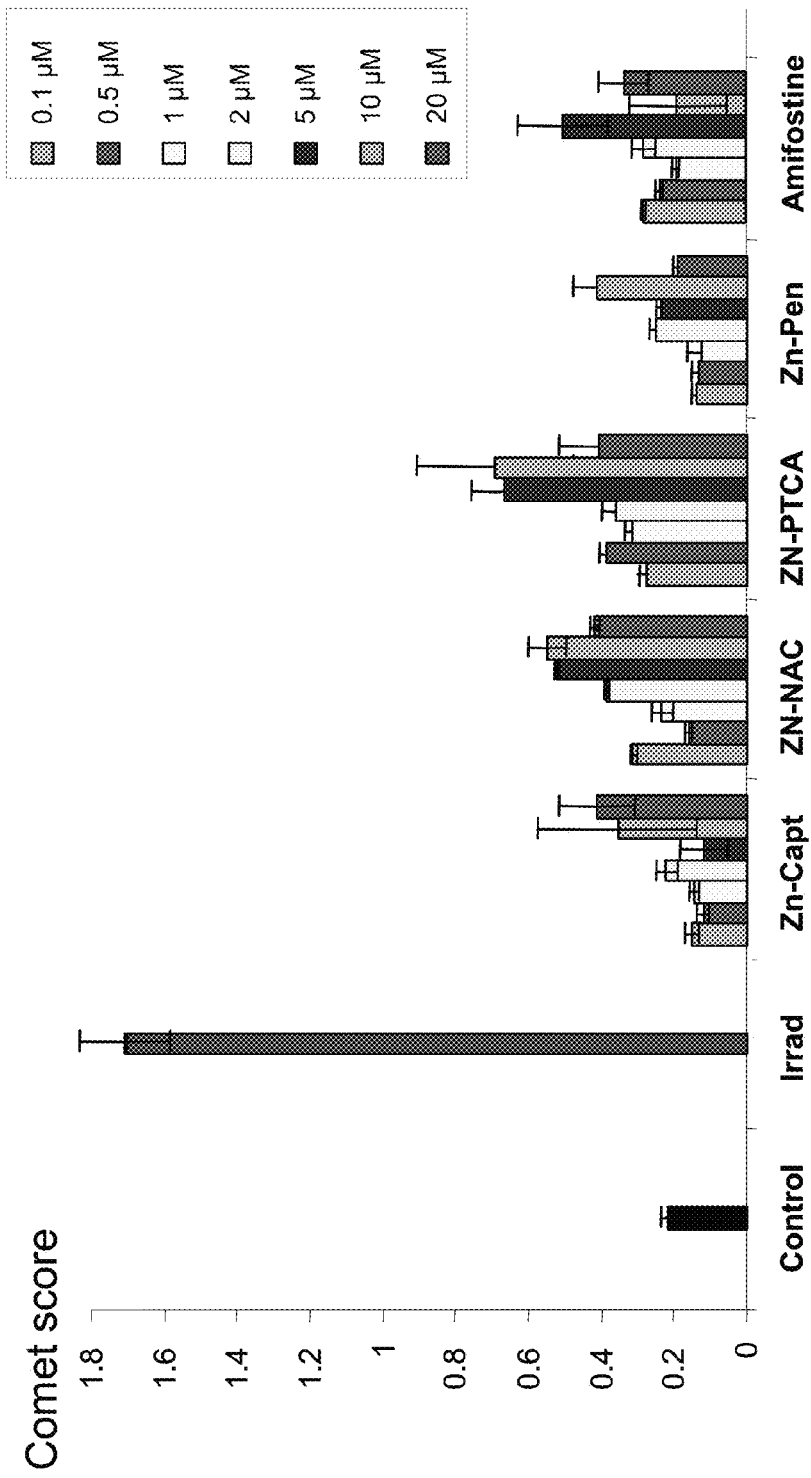

These experiments revealed that DNA degradation occurred in U937 cells after irradiation with 4 Gy, but the (visual) comets were absent if the cells were irradiated in the presence of a $Zn^{2+}$-chelate or amifostine (FIG. 9A). Quantification of the data showed that radioprotection could be achieved even at $Zn^{2+}$-chelate doses as low as 0.1 µM (FIG. 9B).

Example 7

Figure 10A:
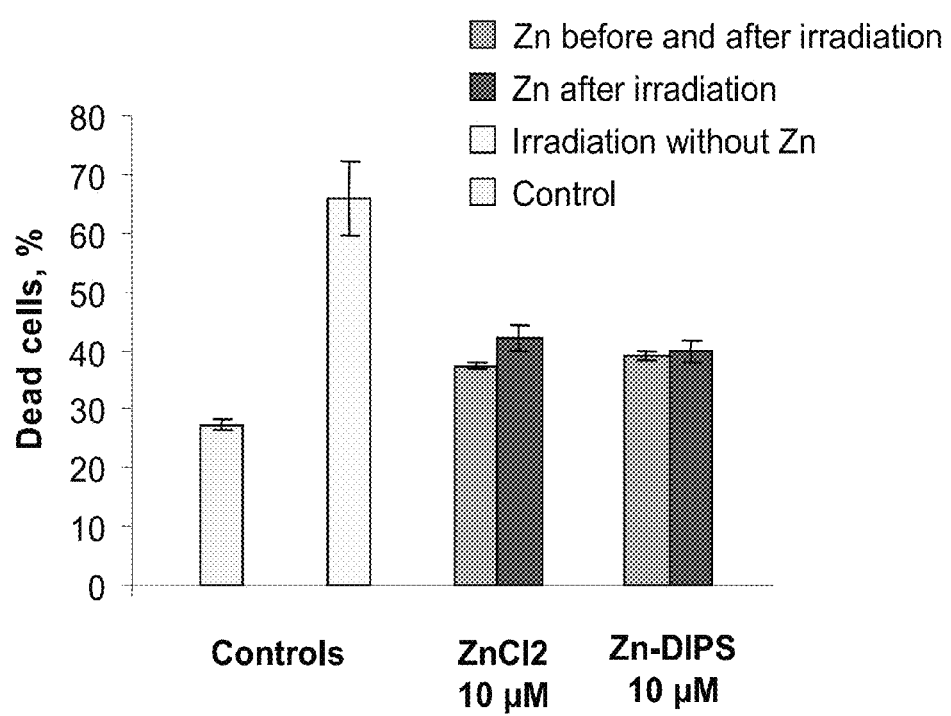
FIG. 10 illustrates cytoprotection against exposure to radiation. (A) Plots radiation-induced thyroid cell death in vitro (450 Gy, LDH release assay). (B) Plots radiation-induced cell death of U937 cells by $Zn^{2+}$-chelates added at different doses after irradiation (4 Gy).
Figure 10B:
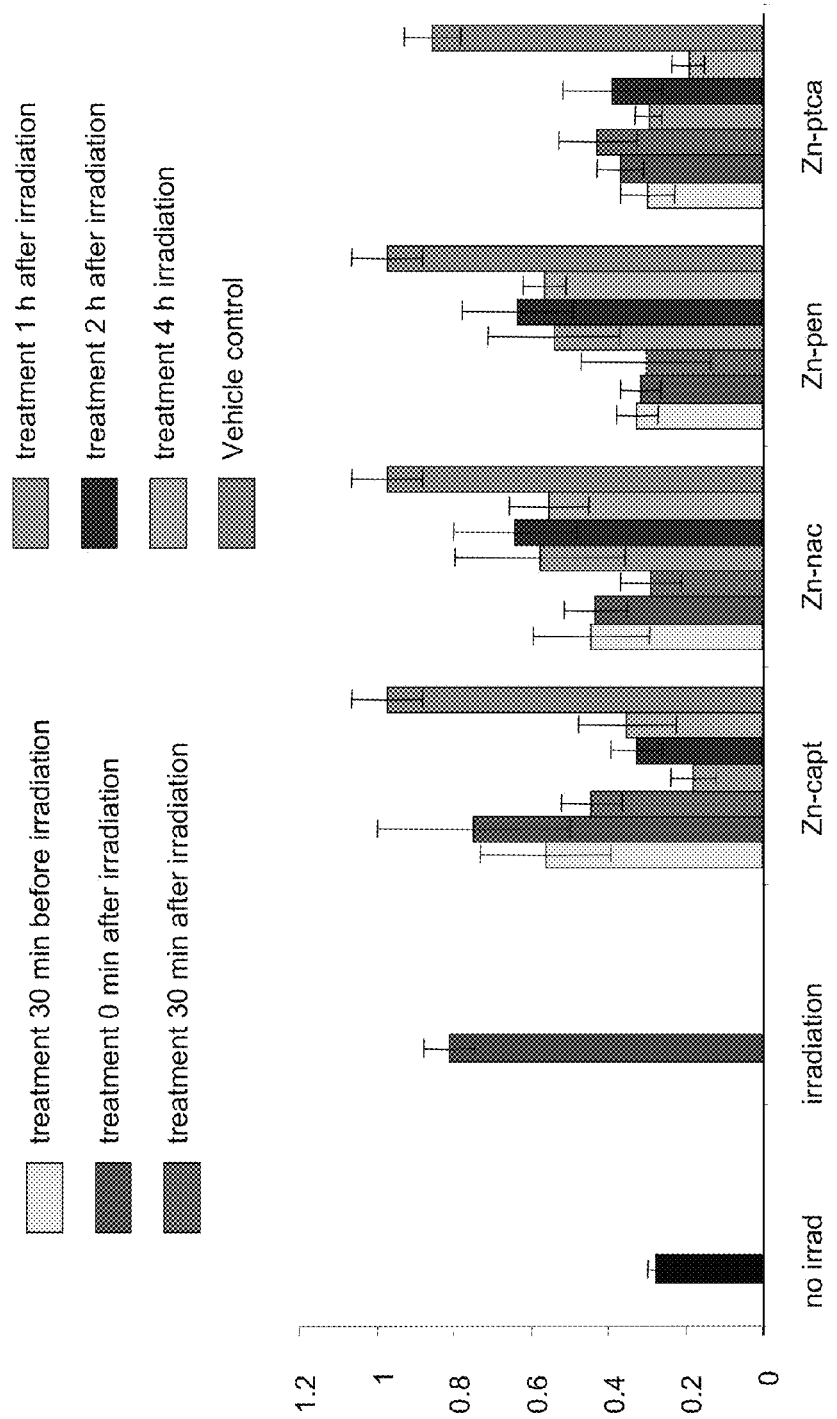

$Zn^{2+}$-Chelates Protect Thyroid Cells from Radiation-Induced Cell Death if Added Before or after High Dose Irradiation FRTL-5 thyroid cells (ATCC, catalog #CRL8305) were irradiated with 450 Gy without or with $Zn^{2+}$-chelates added before and/or after irradiation. Cell death was measured 24 hr after irradiation using a LDH release assay or a Comet assay. Zn-DIPS provided protection even when added after radiation (FIG. 10A). In another experiment, $Zn^{2+}$-chelates (i.e., Zn-captopril, Zn-NAC, Zn-penicillamine, or Zn-PTCA) were added to human U937 cells either 30 minutes before, immediately after, or up to 4 hours after irradiation (4 Gy). It was again found that $Zn^{2+}$-chelates protected against radiation injury if added long after irradiation (FIG. 10B).

Example 8

$Zn^{2+}$-Chlelates But Not Ligands Provide Radioprotection In Vitro

Human U937 cells were irradiated in vitro with 50 Gy and the compounds were added at different concentrations (0-100

μM) immediately after irradiation. The following compounds were tested: ZnCl₂ as a positive control, cysteine, NAC, Zn-cysteine, and Zn-NAC). Cell death was measured 24 hr after irradiation using a PI assay (as detailed above).

Figure 11:
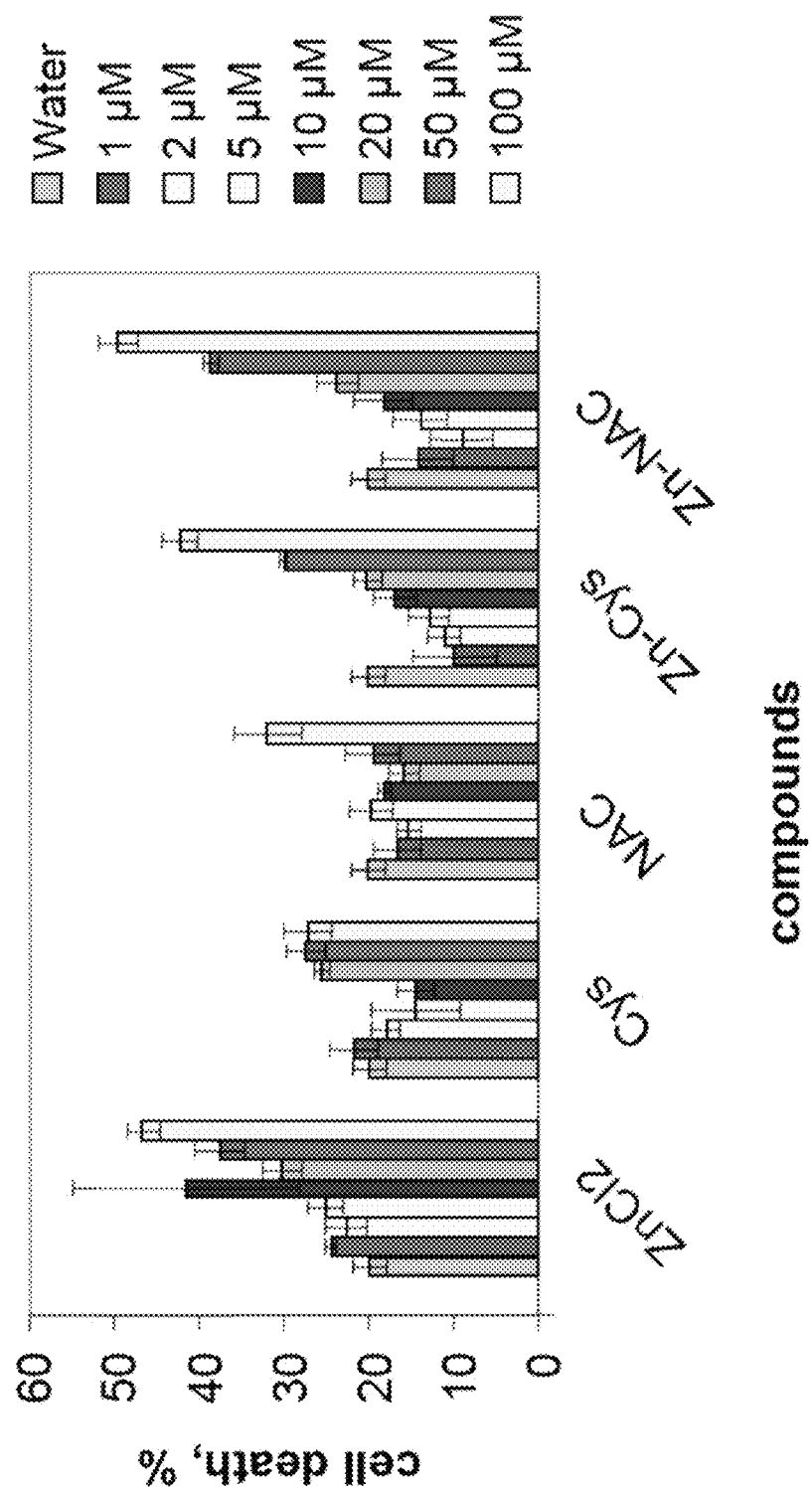
FIG. 11 illustrates radioprotection provided by different concentrations of zinc chelates added to U937 cells irradiated with 50 Gy. N=4 per group.

As shown in FIG. 11, ZnCl₂ was rather cytotoxic and did not provide any radioprotection. Cysteine and NAC are not cytotoxic and not cytoprotective. In contrast, Zn-cysteine and Zn-NAC provide significant cytoprotection when added after irradiation. Furthermore, the Zn⁺-chelates provide cytoprotection at very low concentrations (i.e., 1-5 μM).

Example 9

Zn²⁺-Chelates Provide Radioprotection In Vivo

Mice were exposed to total body irradiation and the radioprotective effects of Zn⁺-chelates administered before or after the irradiation were examined. Each unanesthetized mouse was placed temporarily in a well ventilated plexiglass restrainer and exposed to total body irradiation from a cesium irradiator. A dose of 8 Gy was chosen on the basis of previous studies utilizing male CD-1 mice (Bichay et al., 1986, supra). A total of 6-10 animals per group were used. The animals were allowed to survive for 36 hr after irradiation.

To test for radioprotective effects, Zn-DIPS was injected subcutaneously twice a day 15 mg/kg each time (i.e., 30 mg/kg/day). One group of animals ("before") received Zn-DIPS starting 2 days before irradiation and continued until 36 hr after irradiation. Another group ("after") was injected with Zn-DIPS about 30 min before irradiation and continued until euthanasia. "Vehicle" control animals were injected with vehicle (i.e., saline) for the duration of the experiment, and irradiated with the same dose.

Figure 12:
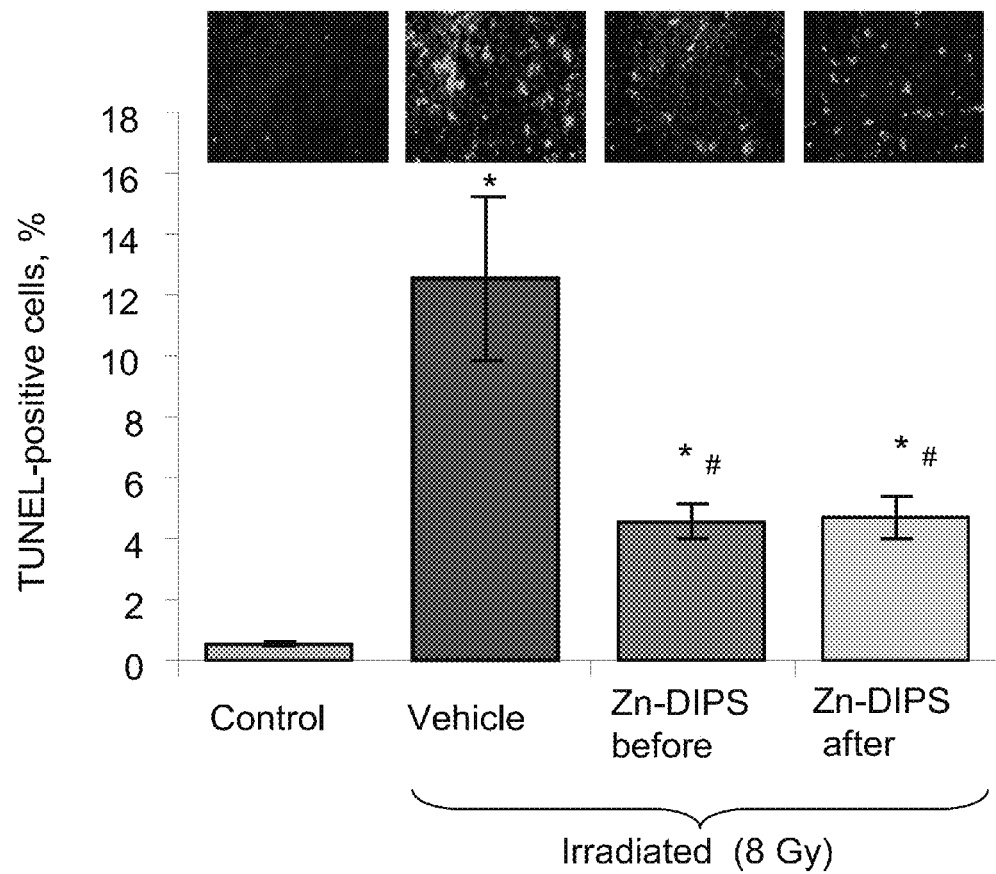
FIG. 12 illustrates that radiation-induced injury of white pulp splenocytes is partially protected by Zn-DIPS injected before or after a single total body irradiation (8 Gy). *P<0.05 compared to control mice, #P<0.05 compared to irradiated vehicle-treated mice. N=6-10 mice per group.

FIG. 12 presents the number of TUNEL-positive cells in white pulp splenocytes from the different groups. Zn-DIPS provided partial radioprotection to mice when administered either before or after a single total body irradiation.

Example 10

Inactivation of DNase I Provides Radioprotection In Vivo

To test the hypothesis that the primary target of a Zn⁺-chelate is apoptotic endonuclease, mice with genetically inactivated DNase I (see Example 1) were exposed to total body irradiation and cell death was measured. Six to eight week old female DNase I knock-out (KO) (DNase −/−) mice and wild type (DNase +/+) mice were irradiated with 8 Gy, and 36 hr later, they were euthanized and select organs (e.g., intestine, bone marrow, and spleen) were harvested and processed for examination. DNA fragmentation and cell death were measured using a TUNEL assay.

Figure 13:
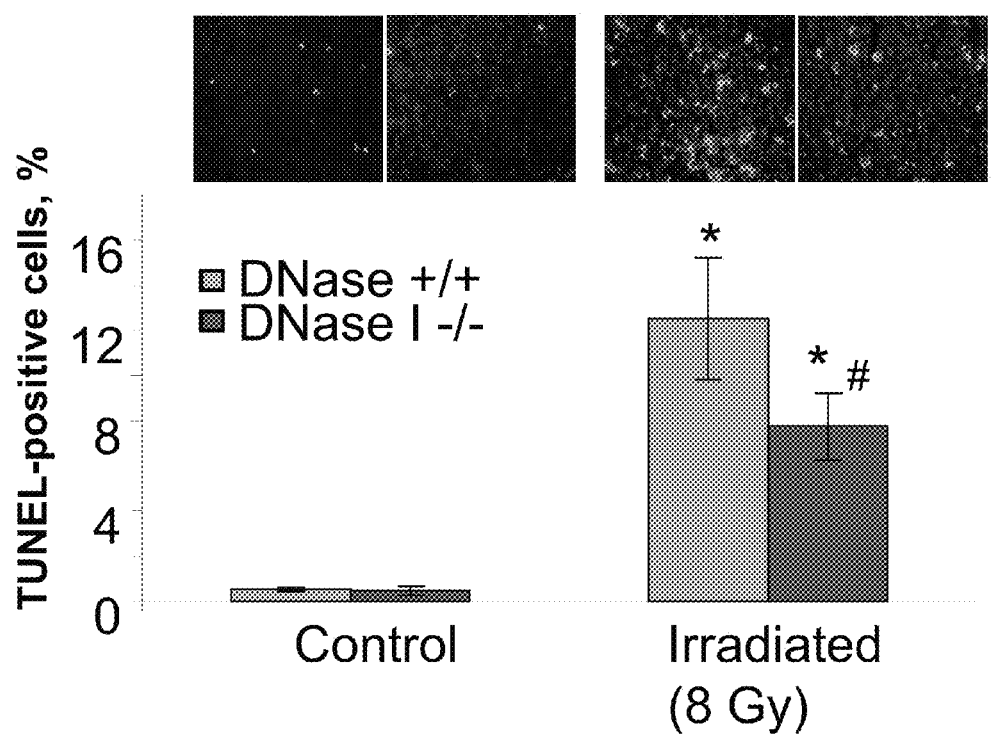
FIG. 13 illustrates that inactivation of endonuclease DNase I provides radioprotection of spleen cells in vivo.
Figure 14:
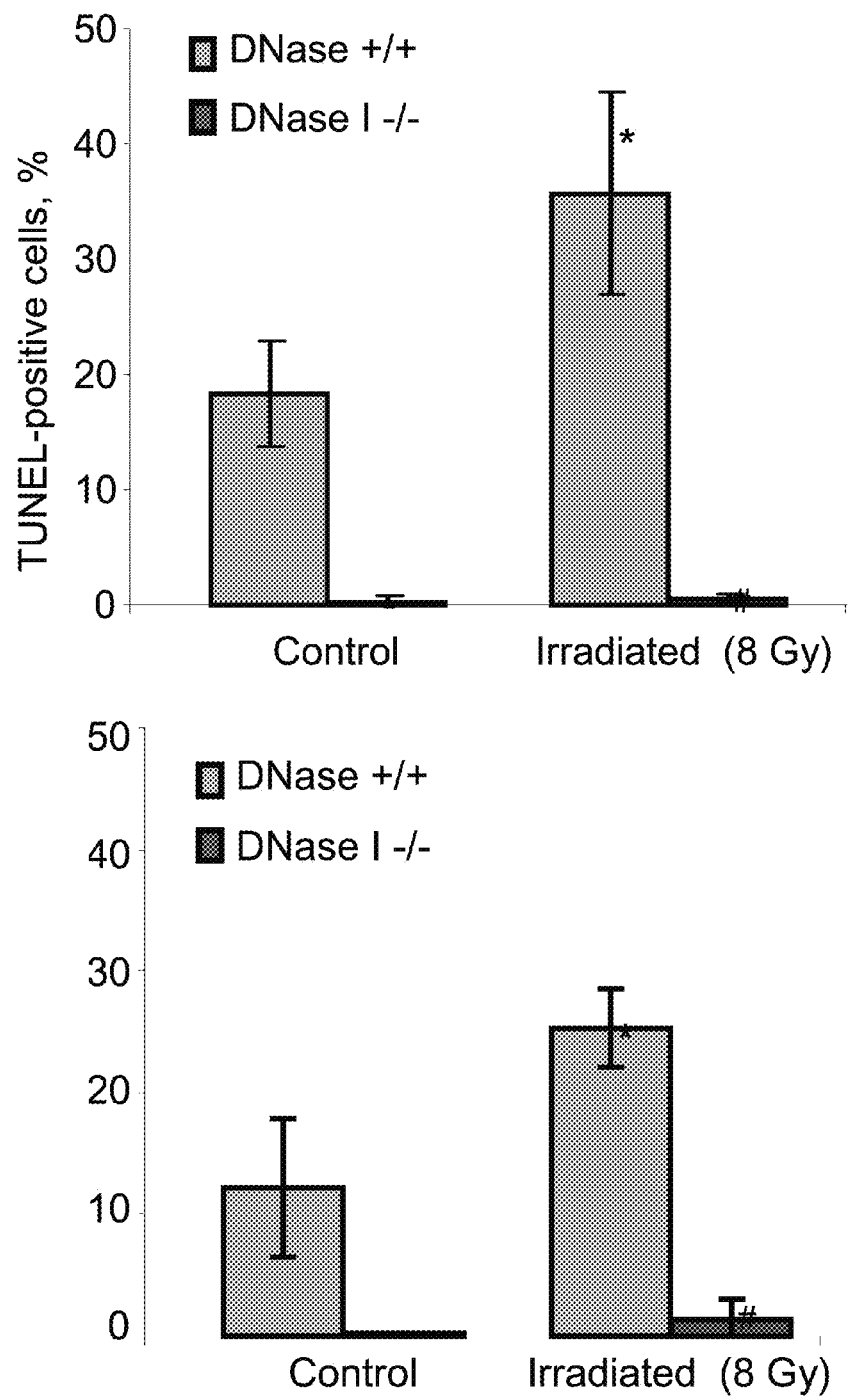
FIG. 14 illustrates that inactivation of endonuclease DNase I provides radioprotection of intestine in vivo.

It was found that DNA fragmentation and cell death were increased by irradiation and that these indicators were lowered in the KO mice relative to wild type mice. Radiation-induced injury of white pulp lymphocytes in spleen was partially ameliorated in the DNase I KO mice (FIG. 13). Since Zn-DIPS provided better protection than inactivation of DNase I (see FIG. 12), it appears that the spleen contains additional targets (such as other endonucleases). In contrast to spleen, radiation-induced injury of intestinal epithelial and stromal cells was minimized to almost zero in DNase I knock-out mice (FIG. 14). These data suggest that DNase I is the only endonuclease in the intestine, and it is responsible for all the endonuclease-mediated DNA fragmentation and cell death in the intestine that is induced by radiation.

What is claimed is:

1. A method for protecting a mammalian cell from a cellular injury, the method comprising contacting the cell with a zinc chelate such that the cell has less damage than a comparable cell not contacted with the zinc chelate, wherein the cellular injury is chosen from chemical injury, thermal injury, ischemia-reperfusion injury, and mechanical trauma, and the zinc chelate comprises at least one zinc ion and at least one ligand selected from the group consisting of a compound comprising Formula (I), a compound comprising Formula (II), captopril, and 3,5-diisopropylsalicylic acid, the compounds comprising Formulas (I) or (II) having the following structures:

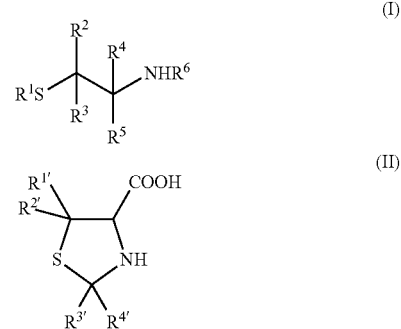

wherein:
R¹ is selected from the group consisting of hydrogen and acyl;
R² and R³ are independently selected from the group consisting of hydrogen, alkyl, alkylamino, carboxyl, carboxylate ester, and carboxamide;
R⁴ and R⁵ are independently selected from the group consisting of hydrogen, alkyl, carboxyl, carboxylate ester, and carboxamide, or together R⁴ and R⁵ form =O;
R⁶ is selected from the group consisting of hydrogen, alkyl, and acyl;
R¹' and R²' are independently selected from the group consisting of hydrogen, alkyl, substituted alkyl, and alkenyl, or together R¹' and R²' form =O; and
R³' and R⁴' are independently selected from the group consisting of hydrogen, alkyl, substituted alkyl, alkenyl, and (CHOH)ₙCH₂OH, or together R³' and R⁴' form =O, wherein n is an integer from 1 to 4.

2. The method of claim 1, wherein the compound comprising Formula (I) is selected from the group consisting of N-acetylcysteine, cysteamine, cysteine, N-(2-mercaptopropionyl)glycine, and penicillamine, and the compound comprising Formula (II) is selected from the group consisting of 2-oxothiazolidine-4-carboxylic acid, 2-n-propylthiazolidine-4-carboxylic acid, 2-(1-ribosyl)thiazolidine-4-carboxylic acid, and thiazolidine-4-carboxylic acid.

3. The method of claim 1, wherein the contacting between the cell and the zinc chelate occurs before the cellular injury.

4. The method of claim 1, wherein the contacting between the cell and the zinc chelate occurs after the cellular injury.

5. The method of claim 1, wherein the cell is within a subject selected from the group consisting of a primate, a companion animal, a zoo animal, and an agricultural animal.

6. The method of claim 1, wherein the cell is within a human.

7. A method for protecting a mammalian cell from a radiation injury, the method comprising contacting the cell with a zinc chelate such that the cell has less damage than a comparable cell not contacted with the zinc chelate, wherein the zinc chelate comprises at least one zinc ion and at least one aminothiol ligand selected from the group consisting N-acetylcysteine, captopril, penicillamine, and a compound comprising Formula (II):

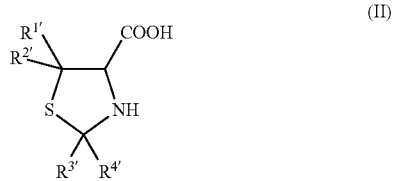

wherein:
R$^{1'}$ and R$^{2'}$ are independently selected from the group consisting of hydrogen, alkyl, substituted alkyl, and alkenyl, or together R$^{1'}$ and R$^{2'}$ form =O; and
R$^{3'}$ and R$^{4'}$ are independently selected from the group consisting of hydrogen, alkyl, substituted alkyl, alkenyl, and (CHOH)$_n$CH$_2$OH, or together R$^{3'}$ and R$^{4'}$ form =O, wherein n is an integer from 1 to 4.

8. The method of claim 7, wherein the radiation is selected from the group consisting of gamma radiation, beta radiation, X-ray radiation, and ultraviolet radiation.

9. The method of claim 7, wherein the compound comprising Formula (II) is selected from the group consisting of 2-(1-ribosyl)thiazolidine-4-carboxylic acid, 2-n-propylthiazolidine-4-carboxylic acid, 2-oxothiazolidine-4-carboxylic acid, and thiazolidine-4-carboxylic acid.

10. The method of claim 7, wherein the zinc chelate is contacted with the cell before the cell is subjected to the radiation.

11. The method of claim 7, wherein the zinc chelate is contacted with the cell after the cell is subjected to the radiation.

12. The method of claim 7, wherein the cell is within a subject selected from the group consisting of a primate, a companion animal, a zoo animal, and an agricultural animal.

13. The method of claim 7, wherein the cell is within a human.

14. The method of claim 12, wherein the zinc chelate is administered to the subject in a route selected from the group consisting of oral, inhalation, transdermal, transmucosal, intravenous, intramuscular, and subcutaneous.

15. The method of claim 12, wherein the zinc chelate is administered to the subject in an oral dosage form.

16. The method of claim 14, wherein the zinc aminothiol zinc chelate is administered to the subject from about 0.5 hour to about 1 hour before exposure to the radiation at a dose of about 0.01 to about 2.5 grams, and administered to the subject every four to six hours after the radiation at a dose of about 0.01 to about 2 grams for about seven days.

17. The method of claim 14, wherein the zinc chelate is administered to the subject from about 0.5 hour to about 1 hour before exposure to the radiation at a dose of about 0.5 grams, and administered to the subject every four to six hours after the radiation at a dose of about 0.25 grams for about seven days.

18. The method of claim 14, wherein the zinc chelate is administered to the subject every four to six hours after the radiation at a dose of about 0.01 to about 2 grams for about seven days.

19. The method of claim 14, wherein the zinc chelate is administered to the subject every four to six hours after the radiation at a dose of about 0.25 grams for about seven days.

20. The method of claim 15, wherein the zinc chelate is coadministered with an agent selected from the group consisting of a buffering agent, a proton pump inhibitor, and a histamine H2 blocker.

21. The method of claim 7, wherein the zinc chelate is zinc-2-(1-ribosyl)thiazolidine-4-carboxylic acid (Zn-RibCys).

22. The method of claim 1, wherein the zinc chelate is zinc-2-(1-ribosyl)thiazolidine-4-carboxylic acid (Zn-RibCys).

23. The method of claim 7, wherein the zinc chelate is selected from the group consisting of zinc-N-acetylcysteine (Zn-NAC), zinc-penicillamine (Zn-penicillamine), zinc-captopril (Zn-captopril), zinc-2-(1-ribosyl)thiazolidine-4-carboxylic acid (Zn-RibCys), and zinc-thiazolidine-4-carboxylic acid (Zn-PTCA).

* * * * *

UNITED STATES PATENT AND TRADEMARK OFFICE
CERTIFICATE OF CORRECTION

| | | |
|---|---|---|
| PATENT NO. | : 8,685,951 B2 | Page 1 of 1 |
| APPLICATION NO. | : 12/055790 | |
| DATED | : April 1, 2014 | |
| INVENTOR(S) | : Basnakian | |

It is certified that error appears in the above-identified patent and that said Letters Patent is hereby corrected as shown below:

In the Specification

Column 1, lines 14 and 15 after "National Institutes of Health" please add -- and GM103429 awarded by the National Institute of General Medical Sciences --.

Signed and Sealed this
Twenty-fourth Day of June, 2014

Michelle K. Lee
*Deputy Director of the United States Patent and Trademark Office*